(12) United States Patent
McHugh et al.

(10) Patent No.: US 12,161,721 B2
(45) Date of Patent: Dec. 10, 2024

(54) PROCESSES FOR THE FORMULATION OF PNEUMOCOCCAL POLYSACCHARIDES FOR CONJUGATION TO A CARRIER PROTEIN

(71) Applicant: Merck Sharp & Dohme LLC, Rahway, NJ (US)

(72) Inventors: Patrick McHugh, Pipersville, PA (US); Michael Albert Winters, Doylestown, PA (US); Janelle Konietzko, Lansdale, PA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 0 days.

(21) Appl. No.: 17/806,107

(22) Filed: Jun. 9, 2022

(65) Prior Publication Data
US 2022/0296723 A1 Sep. 22, 2022

Related U.S. Application Data

(62) Division of application No. 16/645,096, filed as application No. PCT/US2018/049311 on Sep. 4, 2018, now Pat. No. 11,400,162.

(60) Provisional application No. 62/555,485, filed on Sep. 7, 2017.

(51) Int. Cl.
*A61K 47/54* (2017.01)
*A61K 47/62* (2017.01)
*C07H 1/00* (2006.01)

(52) U.S. Cl.
CPC .......... *A61K 47/549* (2017.08); *A61K 47/62* (2017.08); *C07H 1/00* (2013.01)

(58) Field of Classification Search
CPC ......... A61K 47/549; A61K 47/62; C07H 1/00
USPC ..................................................... 536/123.1
See application file for complete search history.

(56) References Cited

U.S. PATENT DOCUMENTS

| | | | |
|---|---|---|---|
| 4,711,779 A | 12/1987 | Porro et al. | |
| 5,623,057 A | 4/1997 | Marburg et al. | |
| 8,192,746 B2 | 6/2012 | Caulfield et al. | |
| 9,283,270 B2 | 3/2016 | Kapre et al. | |
| 2005/0106181 A1 | 5/2005 | Constantino | |
| 2007/0231340 A1* | 10/2007 | Hausdorff | A61K 39/092 530/322 |
| 2010/0316666 A1 | 12/2010 | Hausdorff et al. | |
| 2015/0190521 A1 | 7/2015 | Biemans et al. | |
| 2015/0216996 A1 | 8/2015 | Gu et al. | |
| 2016/0022798 A1 | 1/2016 | Freese et al. | |
| 2016/0324950 A1 | 11/2016 | Anderson et al. | |
| 2017/0021006 A1 | 1/2017 | Watson et al. | |
| 2018/0333484 A1* | 11/2018 | Fairman | A61P 37/00 |

FOREIGN PATENT DOCUMENTS

| | | |
|---|---|---|
| CA | 2153733 A1 | 1/1997 |
| CN | 1993141 A | 7/2007 |
| CN | 101460193 A | 6/2009 |
| EA | 200801344 A1 | 12/2008 |
| EP | 0497524 A2 | 8/1992 |
| JP | 11506110 A | 6/1999 |
| WO | 1996040225 A1 | 12/1996 |
| WO | 2005120563 A2 | 12/2005 |
| WO | 2007068907 A2 | 6/2007 |
| WO | 2016178123 A1 | 11/2016 |
| WO | 2018144438 A1 | 8/2018 |
| WO | 2018144439 A1 | 8/2018 |
| WO | 2018156465 A1 | 8/2018 |
| WO | 2018156467 A1 | 8/2018 |
| WO | 2018156468 A1 | 8/2018 |
| WO | 2018156491 A1 | 8/2018 |
| WO | 2019036313 A1 | 2/2019 |
| WO | 2019050813 A1 | 3/2019 |
| WO | 2019050814 A1 | 3/2019 |
| WO | 2019050815 A1 | 3/2019 |
| WO | 2019050816 A1 | 3/2019 |
| WO | 2019050818 A1 | 3/2019 |
| WO | 2019083865 A1 | 5/2019 |

OTHER PUBLICATIONS

Johannis P. Kamerling, Pneumococcal polysaccharides: a chemical view, *Streptococcus pneumoniae* molecular biology & mechanisms of disease, 2000, 81-114, -, in Tomasz A (ed), Mary Ann Liebert, Inc.
K. Aaron Geno, Pneumococcal Capsules and Their Types: Past, Present, and Future, Clinical Microbiology Reviews, 2015, 871-899, 28.
U.S. Appl. No. 16/645,096, filed Mar. 6, 2020.
Yu, Kang et al., Synthesis of the biological repeating unit of Streptococcus pneumoniae serotype 23F capsular polysaccharide, Org. Biomol. Chem.,, 14, 11462-11472, 2016.

* cited by examiner

*Primary Examiner* — Yih-Horng Shiao
(74) *Attorney, Agent, or Firm* — Matthew A. Leff; Alysia A. Finnegan

(57) ABSTRACT

The present invention provides a number of process improvements related to the conjugation of capsular polysaccharides from *Streptococcus pneumoniae* to a carrier protein. These process are serotype specific and include acid hydrolysis, addition of sodium chloride to the reductive amination reaction, and addition of sucrose to dissolve polysaccharides. Polysaccharide-protein conjugates prepared using the processes of the invention can be included in multivalent pneumococcal conjugate vaccines.

7 Claims, 3 Drawing Sheets

PROCESSES FOR THE FORMULATION OF PNEUMOCOCCAL POLYSACCHARIDES FOR CONJUGATION TO A CARRIER PROTEIN

CROSS REFERENCE TO RELATED APPLICATIONS

This application is a divisional of U.S. application Ser. No. 16/645,096, filed on Mar. 6, 2020, which is a National Stage application of International Patent Application No. PCT/US2018/049311, filed Sep. 4, 2018, which claims priority to U.S. Provisional Patent Application No. 62/555,485, filed Sep. 7, 2017.

FIELD OF INVENTION

The present invention provides a number of process improvements related to the conjugation of capsular polysaccharides from *Streptococcus pneumoniae* to a carrier protein. Polysaccharide-protein conjugates prepared using the processes of the invention can be included in multivalent pneumococcal conjugate vaccines.

BACKGROUND OF THE INVENTION

*Streptococcus pneumoniae*, one example of an encapsulated bacterium, is a significant cause of serious disease world-wide. In 1997, the Centers for Disease Control and Prevention (CDC) estimated there were 3,000 cases of pneumococcal meningitis, 50,000 cases of pneumococcal bacteremia, 7,000,000 cases of pneumococcal otitis media and 500,000 cases of pneumococcal pneumonia annually in the United States. See Centers for Disease Control and Prevention, MMWR Morb Mortal Wkly Rep 1997, 46(RR-8):1-13. Furthermore, the complications of these diseases can be significant with some studies reporting up to 8% mortality and 25% neurologic sequelae with pneumococcal meningitis. See Arditi et al., 1998, Pediatrics 102:1087-97.

The multivalent pneumococcal polysaccharide vaccines that have been licensed for many years have proved invaluable in preventing pneumococcal disease in adults, particularly, the elderly and those at high-risk. However, infants and young children respond poorly to unconjugated pneumococcal polysaccharides. Bacterial polysaccharides are T-cell-independent immunogens, eliciting weak or no response in infants. Chemical conjugation of a bacterial polysaccharide immunogen to a carrier protein converts the immune response to a T-cell-dependent one in infants. Diphtheria toxoid (DTx, a chemically detoxified version of DT) and CRM197 have been described as carrier proteins for bacterial polysaccharide immunogens due to the presence of T-cell-stimulating epitopes in their amino acid sequences.

The pneumococcal conjugate vaccine, Prevnar®, containing the 7 most frequently isolated serotypes (4, 6B, 9V, 14, 18C, 19F and 23F) causing invasive pneumococcal disease in young children and infants at the time, was first licensed in the United States in February 2000. Following universal use of Prevnar® in the United States, there has been a significant reduction in invasive pneumococcal disease in children due to the serotypes present in Prevnar®. See Centers for Disease Control and Prevention, MMWR Morb Mortal Wkly Rep 2005, 54(36):893-7. However, there are limitations in serotype coverage with Prevnar® in certain regions of the world and some evidence of certain emerging serotypes in the United States (for example, 19A and others). See O'Brien et al., 2004, Am J Epidemiol 159:634-44; Whitney et al., 2003, N Engl J Med 348:1737-46; Kyaw et al., 2006, N Engl J Med 354:1455-63; Hicks et al., 2007, J Infect Dis 196:1346-54; Traore et al., 2009, Clin Infect Dis 48:S181-S189.

Prevnar 13® is a 13-valent pneumococcal polysaccharide-protein conjugate vaccine including serotypes 1, 3, 4, 5, 6A, 6B, 7F, 9V, 14, 18C, 19A, 19F and 23F. See, e.g., U.S. Patent Application Publication No. US 2006/0228380 A1, Prymula et al., 2006, Lancet 367:740-48 and Kieninger et al., Safety and Immunologic Non-inferiority of 13-valent Pneumococcal Conjugate Vaccine Compared to 7-valent Pneumococcal Conjugate Vaccine Given as a 4-Dose Series in Healthy Infants and Toddlers, presented at the 48$^{th}$ Annual ICAAC/ISDA 46$^{th}$ Annual Meeting, Washington DC, Oct. 25-28, 2008. See, also, Dagan et al., 1998, Infect Immun. 66: 2093-2098 and Fattom, 1999, Vaccine 17:126.

The current multivalent pneumococcal conjugate vaccines have been effective in reducing the incidence of pneumococcal disease associated with those serotypes present in the vaccines. However, the prevalence of the pneumococci expressing serotypes not present in the vaccine has been increasing. The process conditions for novel serotypes has to be determined for each serotype for conjugation efficiency and for certain serotypes presented unique challenges. Accordingly, there is a need for improved process conditions for conjugating novel pneumococcal serotypes for inclusion in future vaccines.

SUMMARY OF THE INVENTION

The present invention provides a number of process changes in the preparation of polysaccharides (Ps) from *Streptococcus pneumoniae* that are unique to specific serotypes. These process changes improve the properties of the polysaccharide and/or the polysaccharide dissolution, resulting in better conjugation.

In one embodiment, the invention provides process conditions for obtaining *S. pneumoniae* polysaccharides from serotypes 12F, 23A, 24F, and 31 of a reduced size, which when conjugated to a carrier protein (Pr) in an aprotic solvent show desired conjugate attributes. Specifically, Ps size reduction of these serotypes by acid hydrolysis yields lower Ps molecular mass for protein conjugation compared to homogenization, which improves conjugate attributes such as lysine consumption, free Ps or free Pr.

In one embodiment, the invention provides process conditions for obtaining improved polysaccharide-protein conjugate attributes after conjugation in an aprotic solvent such as DMSO using sodium chloride, particularly for *S. pneumoniae* polysaccharides from serotypes 15A, 16F, 17F, 20, 24F, and 35B. Specifically, in this embodiment, inclusion of ≥1 mM sodium chloride prior to or during the conjugation reaction (regardless of where in the process the sodium chloride is added) results in improved conjugate attributes such as larger conjugate size, higher lysine consumption, lower free Ps or free Pr.

In one embodiment, the invention provides a range of pre-lyophilization formulation conditions for *S. pneumoniae* polysaccharides of serotypes 3, 8, and 24F to ensure complete dissolution following lyophilization. Specifically, polysaccharides are formulated with sucrose and water, such that the sucrose to polysaccharide mass ratio is ≥30×, and optimally ≥40×. For example, for a given pre-lyophilization polysaccharide concentration of 2 mg Ps/mL, sucrose concentration should minimally be 60 mg sucrose/mL (6% w/v sucrose), and optimally be ≥80 mg sucrose/mL (8% w/v sucrose), for dissolution following lyophilization.

Polysaccharides formulated in these ways allows conjugation with proteins following lyophilization and redissolution resulting in the desired properties.

DETAILED DESCRIPTION OF THE INVENTION

Figure 1:
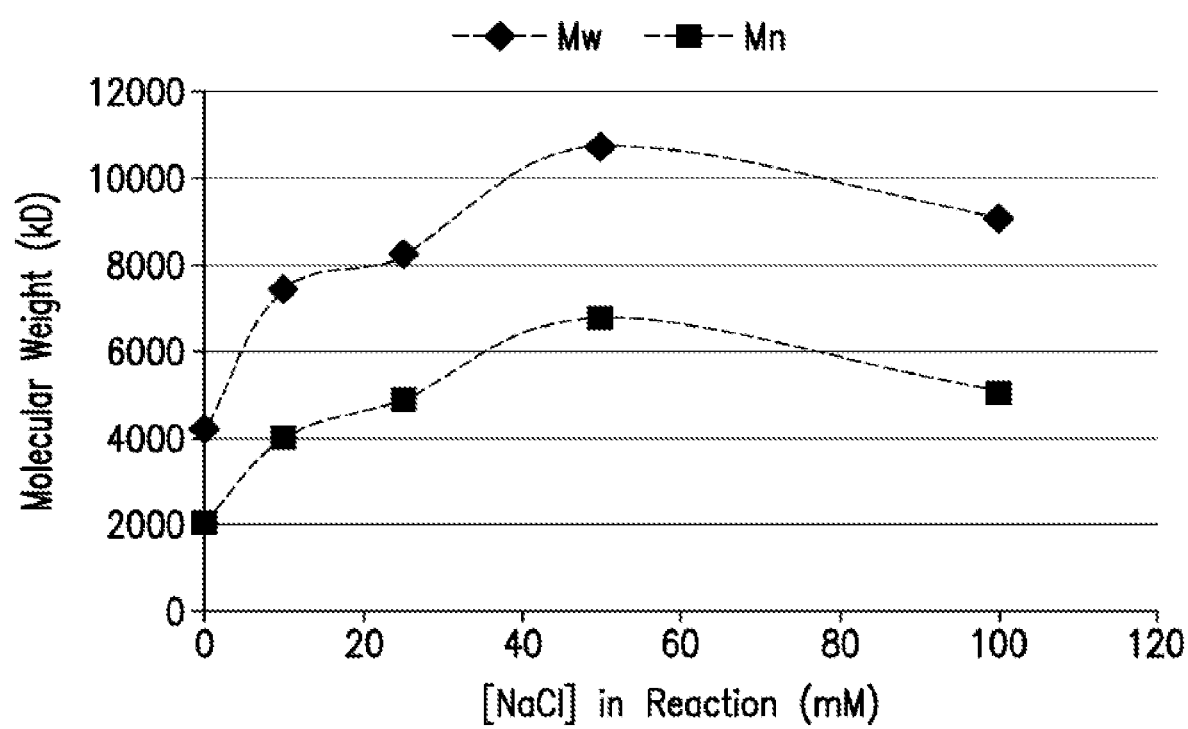
FIG. 1 demonstrates the impact of sodium chloride on conjugate size for S. pneumoniae polysaccharide from serotype 20.

The present invention provides a number of process changes in the preparation of polysaccharides (Ps) from Streptococcus pneumoniae that are unique to specific serotypes. These process changes improve the properties of the polysaccharide and/or the polysaccharide dissolution, resulting in better conjugation.

The inventors have discovered that size reduction of certain S. pneumoniae polysaccharides by acid hydrolysis prior to protein conjugation yields improved conjugate attributes as shown in the Examples. Without being bound by any particular theory, one possible mechanism for the use of acid hydrolysis that might explain the observed behavior is that conjugating with lower molecular mass Ps from acid hydrolysis provides less steric hindrance between Ps and Pr molecules during the conjugation reaction, which may in turn lead to enhanced interaction and improved conjugation.

The inventors have discovered that complete dissolution of certain S. pneumoniae polysaccharides required the presence of sucrose following lyophilization, as shown in the Examples. Without being bound by any particular theory, one possible mechanism for the use of sucrose that might explain the observed dissolution behavior is that some polysaccharide serotypes, due to their chemical structure, self-associate more readily than others during lyophilization or dissolution, and that higher sucrose/polysaccharide ratios inhibit self-association, permitting dissolution following lyophilization.

The inventors have discovered that inclusion of ≥1 mM sodium chloride prior to or during the conjugation reaction, particularly for S. pneumoniae polysaccharides from serotypes 16F, 20, and 24F, (regardless of where in the process the sodium chloride is added) results in improved conjugate attributes such as larger conjugate size, higher lysine consumption, lower free Ps or free Pr, as shown in the Examples. Without being bound by any particular theory, one possible mechanism for the use of sodium chloride that might explain the observed conjugation behavior for sodium chloride is that for some polysaccharide serotypes, due to their chemical structure and charge distribution, sodium chloride provides electrostatic shielding, allowing enhanced interaction with proteins and leading to improved conjugation. Sodium chloride also provides additional ionic strength to the reaction mixture, which may reduce the exposure of the hydrophobic region of carrier proteins, thereby reducing protein aggregation.

As used herein, the term "polysaccharide" (Ps) is meant to include any antigenic saccharide element (or antigenic unit) commonly used in the immunologic and bacterial vaccine arts, including, but not limited to, a "saccharide", an "oligosaccharide", a "polysaccharide", a "liposaccharide", a "lipo-oligosaccharide (LOS)", a "lipopolysaccharide (LPS)", a "glycosylate", a "glycoconjugate", a "derivatized or activated polysaccharide or oligosaccharide", and the like. Unless otherwise specified, the polysaccharide nomenclature used herein follows the IUB-IUPAC Joint Commission on Biochemical Nomenclature (JCBM) Recommendations 1980. See JCBN, 1982, J. Biol. Chem. 257:3352-3354.

As used herein, "immunogenic composition" refers to a composition containing an antigen, such as a bacterial capsular polysaccharide or a polysaccharide-protein conjugate, that has the ability to elicit an immune response in a host such as a mammal, either humorally or cellularly mediated, or both. The immunogenic composition may serve to sensitize the host by the presentation of the antigen in association with MHC molecules at a cell surface. In addition, antigen-specific T-cells or antibodies can be generated to allow for the future protection of an immunized host. Immunogenic compositions thus can protect the host from infection by the bacteria, reduced severity, or may protect the host from death due to the bacterial infection. Immunogenic compositions may also be used to generate polyclonal or monoclonal antibodies, which may be used to confer passive immunity to a subject. Immunogenic compositions may also be used to generate antibodies that are functional as measured by the killing of bacteria in either an animal efficacy model or via an opsonophagocytic killing assay.

As used herein, the term "isolated" in connection with a polysaccharide refers to isolation of S. pneumoniae serotype specific capsular polysaccharide from purified polysaccharide using purification techniques known in the art, including the use of centrifugation, depth filtration, precipitation, ultrafiltration, treatment with activate carbon, diafiltration and/or column chromatography. Generally an isolated polysaccharide refers to partial removal of proteins, nucleic acids and non-specific endogenous polysaccharide (C-polysaccharide). The isolated polysaccharide contains less than 10%, 8%, 6%, 4%, or 2% protein impurities and/or nucleic acids. The isolated polysaccharide contains less than 20% of C-polysaccharide with respect to type specific polysaccharides.

As used herein, the term "purified" in connection with a bacterial capsular polysaccharide refers to the purification of the polysaccharide from cell lysate through means such as centrifugation, precipitation, and ultra-filtration. Generally, a purified polysaccharide refers to removal of cell debris and DNA.

As used herein, the term "Mw" refers to the weight averaged molecular weight and is typically expressed in Da or kDa. Mw takes into account that a bigger molecule contains more of the total mass of a polymer sample than the smaller molecules do. Mw can be determined by techniques such as static light scattering, small angle neutron scattering, X-ray scattering, and sedimentation velocity.

As used herein, the term "Mn" refers to a number average molecular weight and is typically expressed in Da or kDa. Mn is calculated by taking the total weight of a sample divided by the number of molecules in the sample and can be determined by techniques such as gel permeation chromatography, viscometry via the (Mark-Houwink equation), colligative methods such as vapor pressure osmometry, end-group determination or proton NMR. Mw/Mn reflects polydispersity.

As used herein, the term "comprises" when used with the immunogenic composition of the invention refers to the inclusion of any other components (subject to limitations of "consisting of" language for the antigen mixture), such as adjuvants and excipients. The term "consisting of" when used with the multivalent polysaccharide-protein conjugate mixture refers to a mixture having those particular *S. pneumoniae* polysaccharide protein conjugates and no other *S. pneumoniae* polysaccharide protein conjugates from a different serotype.

Unless otherwise specified, all ranges provided herein are inclusive of the recited lower and upper limits.

Capsular Polysaccharides

Capsular polysaccharides from *Streptococcus pneumoniae* from the serotype(s) of the invention (e.g., serotypes 23A, 24F and 31) can be prepared by standard techniques known to those skilled in the art. For example, polysaccharides can be isolated from bacteria and may be sized to some degree by known methods (see, e.g., European Patent Nos. EP497524 and EP497525); and preferably by microfluidisation accomplished using a homogenizer or by chemical hydrolysis. In one embodiment, *S. pneumoniae* strains corresponding to each polysaccharide serotype are grown in a soy-based medium. The individual polysaccharides are then purified through standard steps including centrifugation, precipitation, and ultra-filtration. See, e.g., U.S. Patent Application Publication No. 2008/0286838 and U.S. Pat. No. 5,847,112. Polysaccharides can be sized in order to reduce viscosity and/or to improve filterability of subsequent conjugated products. Chemical hydrolysis may be conducted using acetic acid. Mechanical sizing may be conducted using High Pressure Homogenization Shearing.

For serotypes 12F, 23A, 24F and 31, it was found that homogenization of polysaccharide from these serotypes did not result in the desired characteristics. See EXAMPLE 3. Acid hydrolysis can be performed by heating the polysaccharide batch to 80-92° C., preferably 90° C. for serotypes other than 12F, adding an acid such as acetic acid, hydrochloric acid, phosphoric acid, citric acid, to a final concentration of 50-200 mM, then incubating for at least 10 minutes, 20 minutes, 30 minutes, 40 minutes, or 50 minutes. In certain embodiments, the acid hydrolysis occurs for up to 90 minutes, up to 150 minutes, or up to 155 minutes. At the end of the incubation period, the batch is neutralized by adding, e.g., concentrated potassium phosphate pH 7 buffer to a final concentration of 400 mM and cooling to ≤22° C. Size-reduced polysaccharide is 0.2-micron filtered and then concentrated and diafiltered against water using a 5-10 kDa NMWC tangential flow ultrafiltration membrane.

In some embodiments, the purified polysaccharides before conjugation have a molecular weight of between 5 kDa and 4,000 kDa. Molecular weight can be calculated by size exclusion chromatography (SEC) combined with multiangle light scattering detector (MALS) and refractive index detector (RI). In other such embodiments, the polysaccharide has an average molecular weight of between 10 kDa and 4,000 kDa; between 50 kDa and 4,000 kDa; between 50 kDa and 3,000 kDa; between 50 kDa and 2,000 kDa; between 50 kDa and 1,500 kDa; between 50 kDa and 1,000 kDa; between 50 kDa and 750 kDa; between 50 kDa and 500 kDa; between 100 kDa and 4,000 kDa; between 100 kDa and 3,000 kDa; 100 kDa and 2,000 kDa; between 100 kDa and 1,500 kDa; between 100 kDa and 1,000 kDa; between 100 kDa and 750 kDa; between 100 kDa and 500 kDa; between 100 and 400 kDa; between 200 kDa and 4,000 kDa; between 200 kDa and 3,000 kDa; between 200 kDa and 2,000 kDa; between 200 kDa and 1,500 kDa; between 200 kDa and 1,000 kDa; or between 200 kDa and 500 kDa. In certain embodiments, the average molecular weight is 50-300 kD.

In certain embodiments, the polysaccharide has between 10 and 10,000, 10 and 5,000, 10 and 4,000, or 10 and 1000 repeating units. In certain aspects, the polysaccharide has between 20 and 400, 30 to 300, 40 to 200, or 50 to 100 repeating units. In certain aspects the polysaccharide has between 40 and 900 repeating units.

Carrier Protein

Polysaccharides from one or more of the *S. pneumoniae* serotypes described herein can be conjugated to a carrier protein to improve immunogenicity in children, the elderly and/or immunocompromised subjects. Where more than one serotype is used in a multivalent composition, the serotypes may be prepared with the same carrier protein or different carrier proteins. Each capsular polysaccharide of the same serotype is typically conjugated to the same carrier protein.

In a particular embodiment of the present invention, CRM197 is used as a carrier protein. CRM197 is a non-toxic variant of diphtheria toxin (DT). The CRM197 carrier protein is a mutant form of DT that is rendered non-toxic by a single amino acid substitution in Fragment A at residue 52. In one embodiment, the CRM197 carrier protein is isolated from cultures of *Corynebacterium diphtheria* strain C7 (□197) grown in casamino acids and yeast extract-based medium. In another embodiment, CRM197 is prepared recombinantly in accordance with the methods described in U.S. Pat. No. 5,614,382. Typically, CRM197 is purified through a combination of ultra-filtration, ammonium sulfate precipitation, and ion-exchange chromatography. In some embodiments, CRM197 is prepared in *Pseudomonas fluorescens* using Pfenex Expression Technology™ (Pfenex Inc., San Diego, CA).

Other suitable carrier proteins include additional inactivated bacterial toxins such as DT, Diphtheria toxoid fragment B (DTFB), TT (tetanus toxid) or fragment C of TT, pertussis toxoid, cholera toxoid (e.g., as described in International Patent Application Publication No. WO 2004/083251), *E. coli* LT (heat-labile enterotoxin), *E. coli* ST (heat-stable enterotoxin), and exotoxin A from *Pseudomonas aeruginosa*. Bacterial outer membrane proteins such as outer membrane complex c (OMPC), porins, transferrin binding proteins, pneumococcal surface protein A (PspA; See International Application Patent Publication No. WO 02/091998), pneumococcal adhesin protein (PsaA), C5a peptidase from Group A or Group B *streptococcus*, or *Haemophilus influenzae* protein D, pneumococcal pneumolysin (Kuo et al., 1995, Infect Immun 63; 2706-13) including ply detoxified in some fashion for example dPLY-GMBS (See International Patent Application Publication No. WO 04/081515) or dPLY-formol, PhtX, including PhtA, PhtB, PhtD, PhtE and fusions of Pht proteins for example PhtDE fusions, PhtBE fusions (See International Patent Application Publication Nos. WO 01/98334 and WO 03/54007), can also be used. Other proteins, such as ovalbumin, keyhole limpet hemocyanin (KLH), bovine serum albumin (BSA) or purified protein derivative of tuberculin (PPD), PorB (from *N. meningitidis*), PD (*Haemophilus influenzae* protein D; see, e.g., European Patent No. EP 0 594 610 B), or immunologically functional equivalents thereof, synthetic peptides (See European Patent Nos. EP0378881 and EP0427347), heat shock proteins (See International Patent Application Publication Nos. WO 93/17712 and WO 94/03208), pertussis proteins (See International Patent Application Publication No. WO 98/58668 and European Patent No. EP0471177), cytokines, lymphokines, growth factors or hormones (See International Patent Application Publication No. WO 91/01146), artificial proteins comprising multiple human CD4+ T cell epitopes from various pathogen derived antigens (See Falugi et al., 2001, Eur J Immunol 31:3816-3824) such as N19 protein (See Baraldoi et al., 2004, Infect Immun 72:4884-7), iron uptake proteins (See International Patent Application Publication No. WO 01/72337), toxin A or B of *C. difficile* (See International Patent Publication No. WO 00/61761), and flagellin (See Ben-Yedidia et al., 1998, Immunol Lett 64:9) can also be used as carrier proteins.

Other DT mutants can also be used as the carrier protein, such as CRM176, CRM228, CRM45 (Uchida et al., 1973, J Biol Chem 218:3838-3844); CRM9, CRM45, CRM102, CRM103 and CRM107 and other mutations described by Nicholls and Youle in Genetically Engineered Toxins, Ed: Frankel, Maecel Dekker Inc, 1992; deletion or mutation of Glu-148 to Asp, Gln or Ser and/or Ala 158 to Gly and other mutations disclosed in U.S. Pat. No. 4,709,017 or 4,950,740; mutation of at least one or more residues Lys 516, Lys 526, Phe 530 and/or Lys 534 and other mutations disclosed in U.S. Pat. No. 5,917,017 or 6,455,673; or fragment disclosed in U.S. Pat. No. 5,843,711.

Where multivalent vaccines are used, a second carrier protein can be used for one or more of the antigens. The second carrier protein is preferably a protein that is non-toxic and non-reactogenic and obtainable in sufficient amount and purity. The second carrier protein is also conjugated or joined with an antigen, e.g., a *S. pneumoniae* polysaccharide to enhance immunogenicity of the antigen. Carrier proteins should be amenable to standard conjugation procedures. In one embodiment, each capsular polysaccharide not conjugated to the first carrier protein is conjugated to the same second carrier protein (e.g., each capsular polysaccharide molecule being conjugated to a single carrier protein). In another embodiment, the capsular polysaccharides not conjugated to the first carrier protein are conjugated to two or more carrier proteins (each capsular polysaccharide molecule being conjugated to a single carrier protein). In such embodiments, each capsular polysaccharide of the same serotype is typically conjugated to the same carrier protein.

Conjugation

Conjugation of pneumococcal polysaccharides to proteins by reductive amination in an aprotic solvent such as DMSO is commonly used. Activated polysaccharides (Ps) and proteins (Pr) are typically lyophilized, resuspended in DMSO, then combined with sodium cyanoborohydride and sodium borohydride added to achieve conjugation. Process details are provided below.

For many pneumococcal serotypes, this process yields conjugates that meet target attributes for size, lysine consumption, free polysaccharide, and free protein. However for some serotypes it was found that target conjugate attributes were more difficult to achieve with this DMSO process, even after optimizing conjugation parameters such as Ps and Pr concentrations and conjugation time. See the EXAMPLES. As described below, the present invention provides several solutions to overcome these issues.

Prior to conjugation, the purified polysaccharides can be chemically activated to make the saccharides capable of reacting with the carrier protein to form an activated polysaccharide. As used herein, the term "activated polysaccharide" refers to a polysaccharide that has been chemically modified as described below to enable conjugation to a linker or a carrier protein. The purified polysaccharides can optionally be connected to a linker. Once activated or connected to a linker, each capsular polysaccharide is separately conjugated to a carrier protein to form a glycoconjugate. The polysaccharide conjugates may be prepared by known coupling techniques.

In certain embodiments, the polysaccharide can be coupled to a linker to form a polysaccharide-linker intermediate in which the free terminus of the linker is an ester group. The linker is therefore one in which at least one terminus is an ester group. The other terminus is selected so that it can react with the polysaccharide to form the polysaccharide-linker intermediate.

In certain embodiments, the polysaccharide can be coupled to a linker using a primary amine group in the polysaccharide. In this case, the linker typically has an ester group at both termini. This allows the coupling to take place by reacting one of the ester groups with the primary amine group in the polysaccharide by nucleophilic acyl substitution. The reaction results in a polysaccharide-linker intermediate in which the polysaccharide is coupled to the linker via an amide linkage. The linker is therefore a bifunctional linker that provides a first ester group for reacting with the primary amine group in the polysaccharide and a second ester group for reacting with the primary amine group in the carrier molecule. A typical linker is adipic acid N-hydroxysuccinimide diester (SIDEA).

In certain embodiments, the coupling can also take place indirectly, i.e. with an additional linker that is used to derivatise the polysaccharide prior to coupling to the linker. The polysaccharide is coupled to the additional linker using a carbonyl group at the reducing terminus of the polysaccharide. This coupling comprises two steps: (a1) reacting the carbonyl group with the additional linker; and (a2) reacting the free terminus of the additional linker with the linker. In these embodiments, the additional linker typically has a primary amine group at both termini, thereby allowing step (a1) to take place by reacting one of the primary amine groups with the carbonyl group in the polysaccharide by reductive amination. A primary amine group is used that is reactive with the carbonyl group in the polysaccharide. Hydrazide or hydroxylamino groups are suitable. The same primary amine group is typically present at both termini of the additional linker. The reaction results in a polysaccharide-additional linker intermediate in which the polysaccharide is coupled to the additional linker via a C—N linkage.

In certain embodiments, the polysaccharide can be coupled to the additional linker using a different group in the polysaccharide, particularly a carboxyl group. This coupling comprises two steps: (a1) reacting the group with the additional linker; and (a2) reacting the free terminus of the additional linker with the linker. In this case, the additional linker typically has a primary amine group at both termini, thereby allowing step (a1) to take place by reacting one of the primary amine groups with the carboxyl group in the polysaccharide by EDAC activation. A primary amine group is used that is reactive with the EDAC-activated carboxyl group in the polysaccharide. A hydrazide group is suitable. The same primary amine group is typically present at both termini of the additional linker. The reaction results in a polysaccharide-additional linker intermediate in which the polysaccharide is coupled to the additional linker via an amide linkage.

In one embodiment, the chemical activation of the polysaccharides and subsequent conjugation to the carrier protein by reductive amination can be achieved by means described in U.S. Pat. Nos. 4,365,170, 4,673,574 and 4,902,506, U.S. Patent Application Publication Nos. 2006/0228380, 2007/184072, 2007/0231340 and 2007/0184071, and International Patent Application Publication Nos.

WO2006/110381, WO2008/079653, and WO2008/143709). The chemistry may entail the activation of pneumococcal polysaccharide by reaction with any oxidizing agent which a primary hydroxyl group to an aldehyde, such as TEMPO in the presence of oxidant (WO2104/097099), or reacting two vicinal hydroxyl groups to aldehydes, such as periodate (including sodium periodate, potassium periodate, or periodic acid). The reactions lead to a random oxidation of primary hydroxyl groups or random oxidative cleavage of vicinal hydroxyl groups of the carbohydrates with the formation of reactive aldehyde groups.

In this embodiment, coupling to the carrier protein is by reductive amination via direct amination to the lysyl groups of the protein. For example, conjugation is carried out by reacting a mixture of the activated polysaccharide and carrier protein with a reducing agent such as sodium cyanoborohydride, optionally in the presence of nickel for aqueous conjugation. The conjugation reaction may take place under aqueous solution or in the presence of dimethylsulfoxide (DMSO). See, e.g., U.S. Patent Application Publication Nos. US2015/0231270 and US2011/0195086 and European Patent No. EP 0471 177 B1. Unreacted aldehydes are then capped with the addition of a strong reducing agent, such as sodium borohydride.

Reductive amination involves two steps, (1) oxidation of the polysaccharide to form reactive aldehydes, (2) reduction of the imine (Schiff base) formed between activated polysaccharide and a carrier protein to form a stable amine conjugate bond. Before oxidation, the polysaccharide is optionally size reduced. Mechanical methods (e.g. homogenization) or chemical hydrolysis may be employed. Chemical hydrolysis may be conducted using acetic acid. The oxidation step may involve reaction with periodate. For the purpose of the present invention, the term "periodate" includes both periodate and periodic acid; the term also includes both metaperiodate ($IO_4^-$) and orthoperiodate ($IO_6^{5-}$) and includes the various salts of periodate (e.g., sodium periodate and potassium periodate). In an embodiment the capsular polysaccharide is oxidized in the presence of metaperiodate, preferably in the presence of sodium periodate ($NaIO_4$). In another embodiment the capsular polysaccharide is oxydized in the presence of orthoperiodate, preferably in the presence of periodic acid.

In an embodiment, the oxidizing agent is a stable nitroxyl or nitroxide radical compound, such as piperidine-N-oxy or pyrrolidine-N-oxy compounds, in the presence of an oxidant to selectively oxidize primary hydroxyls (as described in, for example, International Patent Application Publication No. WO 2014/097099). In said reaction, the actual oxidant is the N-oxoammonium salt, in a catalytic cycle. In an aspect, said stable nitroxyl or nitroxide radical compound are piperidine-N-oxy or pyrrolidine-N-oxy compounds. In an aspect, said stable nitroxyl or nitroxide radical compound bears a TEMPO (2,2,6,6-tetramethyl-1-piperidinyloxy) or a PROXYL (2,2,5,5-tetramethyl-1-pyrrolidinyloxy) moiety. In an aspect, said stable nitroxyl radical compound is TEMPO or a derivative thereof. In an aspect, said oxidant is a molecule bearing a N-halo moiety. In an aspect, said oxidant is selected from the group consisting of N-Chloro-Succinimide, N-Bromosuccinimide, N-Iodosuccinimide, Dichloroisocyanuric acid, 1,3,5-trichloro-1,3,5-triazinane-2,4,6-trione, Dibromoisocyanuric acid, 1,3,5-tribromo-1,3,5-triazinane-2,4,6-trione, Diiodoisocyanuric acid and 1,3,5-triiodo-1,3,5-triazinane-2,4,6-trione. Preferably said oxidant is N-Chlorosuccinimide.

In certain aspects, the oxidizing agent is 2,2,6,6-Tetramethyl-1-piperidinyloxy (TEMPO) free radical and N-Chlorosuccinimide (NCS) as the cooxidant (as described in International Patent Application Publication No. WO2014/097099). Therefore in one aspect, the glycoconjugates from S. pneumoniae are obtainable by a method comprising the steps of: a) reacting a saccharide with 2,2,6,6-tetramethyl-1-piperidinyloxy (TEMPO) and N-chlorosuccinimide (NCS) in an aqueous solvent to produce an activated saccharide; and b) reacting the activated saccharide with a carrier protein comprising one or more amine groups (said method is designated "TEMPO/NCS-reductive amination" thereafter).

Optionally the oxidation reaction is quenched by addition of a quenching agent. The quenching agent maybe selected from vicinal diols, 1,2-aminoalcohols, amino acids, glutathione, sulfite, bisulfate, dithionite, metabisulfite, thiosulfate, phosphites, hypophosphites or phosphorous acid (such as glycerol, ethylene glycol, propan-1,2-diol, butan-1,2-diol or butan-2,3-diol, ascorbic acid).

The second step of the conjugation process for reductive amination is the reduction of the imine (Schiff base) bond between activated polysaccharide and a carrier protein to form a stable conjugate bond (so-called reductive amination), using a reducing agent. Reducing agents which are suitable include the cyanoborohydrides (such as sodium cyanoborohydride) or sodium borohydride. In one embodiment the reducing agent is sodium cyanoborohydride.

In certain embodiments of the methods of the invention, the reductive amination reaction is carried out in aprotic solvent (or a mixture of aprotic solvents). In an embodiment, the reduction reaction is carried out in DMSO (dimethylsulfoxide) or in DMF (dimethylformamide) solvent. The DMSO or DMF solvent may be used to reconstitute the activated polysaccharide and carrier protein, if lyophilized. In one embodiment, the aprotic solvent is DMSO.

Sucrose at up to 5%, at a sucrose:Ps mass ratio of 25×, has been used to achieve optimal dissolution in DMSO following lyophilization. See, e.g., International Patent Application Publication No. WO2017/013548. For S. pneumoniae polysaccharides obtained from serotypes 3, 8 and 24F, it was found that higher levels of sucrose were needed to adequately dissolve the polysaccharide prior to protein conjugation in an aprotic solvent. In some embodiments, for these serotypes, sucrose concentrations greater than 5% in an aqueous solution are used. In some embodiments, for these serotypes, sucrose:Ps mass ratios greater than 25× are used, e.g., at least 30×, at least 35×, or at least 40×. In some embodiments, the pre-lyophilization mass ratio of sucrose to polysaccharide is greater than or equal to 30, 31, 32, 33, 34, 35, 36, 37, 38, 39, 40, 45, 50 or more. Other sugars such as trehalose or mannitol can be used.

It was also found that the presence of sodium chloride (NaCl) in the protein conjugation process, whether in an aqueous solution or an aprotic solvent, can be used to reduce the free protein levels, increase conjugate molecular weight, lower free polysaccharide and/or increase lysine consumption for S. pneumoniae polysaccharides purified from serotypes 15A, 16F, 17F, 20, 23A, 24F, and 35B. Thus, the present invention can be directed to a method for preparing a polysaccharide protein conjugate, the method comprising reacting a S. pneumoniae polysaccharide within a first solution with a protein within a second solution to form a third solution in which the polysaccharide protein conjugate reaction takes place to form the polysaccharide protein conjugate, wherein the third solution comprises at least 1 mM salt.

The sodium chloride can be added anywhere in the conjugation process from the preparation of polysaccharide and protein for lyophilization prior to the conjugation reaction to the conjugation reaction itself, e.g., during the Schiff base reaction or during the reductive amination in the presence of sodium cyanoborohydride. In some embodiments, the polysaccharide and protein are separately lyophilized and the salt can be added to either the polysaccharide solution (first solution) or the protein solution (second solution) or both. In some embodiments, the polysaccharide and protein are lyophilized from the same solution to which a salt is added (i.e., the first and second solution are the same). In some embodiments, the salt is added into the solution in which the polysaccharide protein conjugate reaction takes place (i.e., the third solution)

Other salts can be used such as other sodium salts, potassium salts such as potassium chloride, lithium salts, magnesium salts and calcium salts. In some embodiments, from 1 mM to 100 mM of sodium chloride is added to the dissolution solution for the polysaccharide or during the Schiff base reaction, or during the reductive amination reaction in the presence of sodium cyanoborohydride. In some embodiments, at least 2, 3, 4, 5, 6, 7, 8, 9 or 10 mM sodium chloride is used. In some aspects of these embodiments, no more than 100, 75, or 50 mM sodium chloride is used.

At the end of the reduction reaction, there may be unreacted aldehyde groups remaining in the conjugates, which may be capped or quenched using a suitable capping or quenching agent. In one embodiment this capping or quenching agent is sodium borohydride (NaBH$_4$). Suitable alternatives include sodium triacetoxyborohydride or sodium or zinc borohydride in the presence of Bronsted or Lewis acids, amine boranes such as pyridine borane, 2-Picoline Borane, 2,6-diborane-methanol, dimethylamine-borane, t-BuMe'PrN-BH$_3$, benzylamine-BH$_3$ or 5-ethyl-2-methylpyridine borane (PEMB) or borohydride exchange resin.

Glycoconjugates prepared using reductive amination in an aprotic solvent are generally used in multivalent pneumococcal protein conjugate vaccines. Thus, in certain embodiments for multivalent compositions where not all the serotypes are prepared in an aprotic solvent, the reduction reaction for the remaining serotypes is carried out in aqueous solvent (e.g., selected from PBS (phosphate buffered saline), MES (2-(N-morpholino)ethanesulfonic acid), HEPES, (4-(2-hydroxyethyl)-1-piperazineethanesulfonic acid), Bis-tris, ADA (N-(2-Acetamido)iminodiacetic acid), PIPES (piperazine-N,N'-bis(2-ethanesulfonic acid)), MOPSO (3-Morpholino-2-hydroxypropanesulfonic acid), BES (N,N-bis(2-hydroxyethyl)-2-aminoethanesulfonic acid), MOPS (3-(N-morpholino)propanesulfonic acid), DIPSO (3-Bis(2-hydroxyethyl) amino-2-hydroxypropane-1-sulfonic acid), MOBS (4-(N-morpholino)butanesulfonic acid), HEPPSO (N-(2-Hydroxyethyl)piperazine-N-(2-hydroxypropanesulfonic acid)), POPSO (Piperazine-1,4-bis(2-hydroxy-3-propanesulfonic acid)), TEA (triethanolamine), EPPS (4-(2-Hydroxyethyl)piperazine-1-propanesulfonic acid), Bicine or HEPB, at a pH between 6.0 and 8.5, 7.0 and 8.0, or 7.0 and 7.5).

In some embodiments, the glycoconjugates of the present invention comprise a polysaccharide having a molecular weight of between 10 kDa and 10,000 kDa. In other such embodiments, the polysaccharide has a molecular weight of between 25 kDa and 5,000 kDa. In other such embodiments, the polysaccharide has a molecular weight of between 50 kDa and 1,000 kDa. In other such embodiments, the polysaccharide has a molecular weight of between 70 kDa and 900 kDa. In other such embodiments, the polysaccharide has a molecular weight of between 100 kDa and 800 kDa. In other such embodiments, the polysaccharide has a molecular weight of between 200 kDa and 600 kDa. In further such embodiments, the polysaccharide has a molecular weight of 100 kDa to 1000 kDa; 100 kDa to 900 kDa; 100 kDa to 800 kDa; 100 kDa to 700 kDa; 100 kDa to 600 kDa; 100 kDa to 500 kDa; 100 kDa to 400 kDa; 100 kDa to 300 kDa; 150 kDa to 1,000 kDa; 150 kDa to 900 kDa; 150 kDa to 800 kDa; 150 kDa to 700 kDa; 150 kDa to 600 kDa; 150 kDa to 500 kDa; 150 kDa to 400 kDa; 150 kDa to 300 kDa; 200 kDa to 1,000 kDa; 200 kDa to 900 kDa; 200 kDa to 800 kDa; 200 kDa to 700 kDa; 200 kDa to 600 kDa; 200 kDa to 500 kDa; 200 kDa to 400 kDa; 200 kDa to 300; 250 kDa to 1,000 kDa; 250 kDa to 900 kDa; 250 kDa to 800 kDa; 250 kDa to 700 kDa; 250 kDa to 600 kDa; 250 kDa to 500 kDa; 250 kDa to 400 kDa; 250 kDa to 350 kDa; 300 kDa to 1,000 kDa; 300 kDa to 900 kDa; 300 kDa to 800 kDa; 300 kDa to 700 kDa; 300 kDa to 600 kDa; 300 kDa to 500 kDa; 300 kDa to 400 kDa; 400 kDa to 1,000 kDa; 400 kDa to 900 kDa; 400 kDa to 800 kDa; 400 kDa to 700 kDa; 400 kDa to 600 kDa; or 500 kDa to 600 kDa. In certain embodiments where acid hydrolysis is employed, the polysaccharide has a molecular weight of between 10 kDa and 200 kDa, 25 kDa and 200 kDa, 50 kDa and 200 kDa, 10 kDa and 150 kDa, 25 kDa and 150 kDa, or 50 kDa and 150 kDa.

Suitable alternative chemistries include the activation of the saccharide with 1-cyano-4-dimethylamino pyridinium tetrafluoroborate (CDAP) to form a cyanate ester. The activated saccharide may thus be coupled directly or via a spacer (linker) group to an amino group on the carrier protein. For example, the spacer could be cystamine or cysteamine to give a thiolated polysaccharide which could be coupled to the carrier via a thioether linkage obtained after reaction with a maleimide-activated carrier protein (for example using GMBS) or a haloacetylated carrier protein (for example using iodoacetimide [e.g. ethyl iodoacetimide HCl] or N-succinimidyl bromoacetate or SIAB, or SIA, or SBAP). Preferably, the cyanate ester (optionally made by CDAP chemistry) is coupled with hexane diamine or adipic acid dihydrazide (ADH) and the amino-derivatised saccharide is conjugated to the carrier protein using carbodiimide (e.g. EDAC or EDC) chemistry via a carboxyl group on the protein carrier. Such conjugates are described in International Patent Application Publication Nos. WO 93/15760, WO 95/08348 and WO 96/29094; and Chu et al., 1983, Infect. Immunity 40:245-256.

Other suitable techniques use carbodiimides, hydrazides, active esters, norborane, p-nitrobenzoic acid, N-hydroxysuccinimide, S—NHS, EDC, TSTU. Many are described in International Patent Application Publication No. WO 98/42721. Conjugation may involve a carbonyl linker which may be formed by reaction of a free hydroxyl group of the saccharide with CDI (See Bethell et al., 1979, J. Biol. Chem. 254:2572-4; Hearn et al., 1981, J. Chromatogr. 218:509-18) followed by reaction with a protein to form a carbamate linkage. This may involve reduction of the anomeric terminus to a primary hydroxyl group, optional protection/deprotection of the primary hydroxyl group, reaction of the primary hydroxyl group with CDI to form a CDI carbamate intermediate and coupling the CDI carbamate intermediate with an amino group on a protein.

Following the conjugation (the reduction reaction and optionally the capping or quenching reaction), the glycoconjugates may be purified (enriched with respect to the amount of polysaccharide-protein conjugate) by a variety of techniques known to the skilled person. These techniques include dialysis, concentration/diafiltration operations, tangential flow filtration, ultrafiltration, precipitation/elution, column chromatography (ion exchange chromatography, multimodal ion exchange chromatography, DEAE, or hydrophobic interaction chromatography), and depth filtration. See, e.g., U.S. Pat. No. 6,146,902. In an embodiment, the glycoconjugates are purified by diafiltration or ion exchange chromatography or size exclusion chromatography.

One way to characterize the glycoconjugates of the invention is by the number of lysine residues in the carrier protein (e.g., CRM197) that become conjugated to the saccharide, which can be characterized as a range of conjugated lysines (degree of conjugation). The evidence for lysine modification of the carrier protein, due to covalent linkages to the polysaccharides, can be obtained by amino acid analysis using routine methods known to those of skill in the art. Conjugation results in a reduction in the number of lysine residues recovered, compared to the carrier protein starting material used to generate the conjugate materials. In a preferred embodiment, the degree of conjugation of the glycoconjugate of the invention is between 2 and 15, between 2 and 13, between 2 and 10, between 2 and 8, between 2 and 6, between 2 and 5, between 2 and 4, between 3 and 15, between 3 and 13, between 3 and 10, between 3 and 8, between 3 and 6, between 3 and 5, between 3 and 4, between 5 and 15, between 5 and 10, between 8 and 15, between 8 and 12, between 10 and 15 or between 10 and 12. In an embodiment, the degree of conjugation of the glycoconjugate of the invention is about 2, about 3, about 4, about 5, about 6, about 7, about 8, about 9, about 10, about 11, about 12, about 13, about 14 or about 15. In a preferred embodiment, the degree of conjugation of the glycoconjugate of the invention is between 7 and 12. In some such embodiments, the carrier protein is CRM197.

The glycoconjugates of the invention may also be characterized by the ratio (weight/weight) of saccharide to carrier protein. In some embodiments, the ratio of polysaccharide to carrier protein in the glycoconjugate (w/w) is between 0.5 and 3.0 (e.g., about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0). In other embodiments, the saccharide to carrier protein ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the saccharide to carrier protein ratio (w/w) is between 0.8 and 1.2. In a preferred embodiment, the ratio of capsular polysaccharide to carrier protein in the conjugate is between 1 and 2. In some such embodiments, the carrier protein is CRM197. The glycoconjugates and immunogenic compositions of the invention may contain free saccharide that is not covalently conjugated to the carrier protein, but is nevertheless present in the glycoconjugate composition. The free saccharide may be non-covalently associated with (i.e., non-covalently bound to, adsorbed to, or entrapped in or with) the glycoconjugate.

In a preferred embodiment, the glycoconjugate comprises less than about 50%, 45%, 40%, 35%, 30%, 25%, 20% or 15% of free polysaccharide compared to the total amount of polysaccharide. In a preferred embodiment the glycoconjugate comprises less than about 25% of free polysaccharide compared to the total amount of polysaccharide. In a preferred embodiment the glycoconjugate comprises less than about 20% of free polysaccharide compared to the total amount of polysaccharide. In a preferred embodiment the glycoconjugate comprises less than about 15% of free polysaccharide compared to the total amount of polysaccharide.

Multivalent Polysaccharide-Protein Conjugate Vaccines

Polysaccharide-protein conjugates prepared using the methods of the invention can be used in multivalent polysaccharide-protein conjugate vaccines. In certain embodiments, multivalent polysaccharide-protein conjugate vaccines comprise S. pneumoniae capsular polysaccharides from one or more of S. pneumoniae serotypes 1, 2, 3, 4, 5, 6A, 6B, 6C, 6D, 7B, 7C, 7F, 8, 9N, 9V, 10A, 11A, 12F, 14, 15A, 15B, 15C, 16F, 17F, 18B, 18C, 19A, 19F, 20, 21, 22A, 22F, 23A, 23B, 23F, 24B, 24F, 27, 28A, 31, 33F, 34, 35A, 35B, 35F, and 38 either as free polysaccharides, a component of a polysaccharide-protein conjugate or a combination thereof, to provide a multivalent pneumococcal vaccine. In certain embodiments, the immunogenic composition comprises, consists essentially of, or consists of S. pneumoniae capsular polysaccharides from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44 S. pneumoniae serotypes individually conjugated to one or more carrier proteins. Preferably, saccharides from a particular serotype are not conjugated to more than one carrier protein.

After the individual glycoconjugates are purified, they are compounded to formulate the immunogenic composition of the present invention. These pneumococcal conjugates are prepared by separate processes and bulk formulated into a single dosage formulation.

Pharmaceutical/Vaccine Compositions

The present invention further provides compositions, including pharmaceutical, immunogenic and vaccine compositions, comprising, consisting essentially of, or alternatively, consisting of any of the polysaccharide S. pneumoniae serotype combinations described above together with a pharmaceutically acceptable carrier and an adjuvant.

Formulation of the polysaccharide-protein conjugates can be accomplished using art-recognized methods. For instance, individual pneumococcal conjugates can be formulated with a physiologically acceptable vehicle to prepare the composition. Examples of such vehicles include, but are not limited to, water, buffered saline, polyols (e.g., glycerol, propylene glycol, liquid polyethylene glycol) and dextrose solutions.

In a preferred formulation, the vaccine composition is formulated in L-histidine buffer with sodium chloride.

As defined herein, an "adjuvant" is a substance that serves to enhance the immunogenicity of an immunogenic composition of the invention. An immune adjuvant may enhance an immune response to an antigen that is weakly immunogenic when administered alone, e.g., inducing no or weak antibody titers or cell-mediated immune response, increase antibody titers to the antigen, and/or lowers the dose of the antigen effective to achieve an immune response in the individual. Thus, adjuvants are often given to boost the immune response and are well known to the skilled artisan. Suitable adjuvants to enhance effectiveness of the composition include, but are not limited to:

(1) aluminum salts (alum), such as aluminum hydroxide, aluminum phosphate, aluminum sulfate, etc.;

(2) oil-in-water emulsion formulations (with or without other specific immunostimulating agents such as muramyl peptides (defined below) or bacterial cell wall components), such as, for example, (a) MF59 (International Patent Application Publication No. WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton, MA), (b) SAF, containing 10% Squalene, 0.4% Tween 80, 5% pluronic-blocked polymer L121, and thr-MDP either microfluidized into a submicron emulsion or vortexed to generate a larger particle size emulsion, (c) Ribi™ adjuvant system (RAS), (Corixa, Hamilton, MT) containing 2% Squalene, 0.2% Tween 80, and one or more bacterial cell wall components from the group consisting of 3-O-deacylated monophosphorylipid A (MPL™) described in U.S. Pat. No. 4,912,094, trehalose dimycolate (TDM), and cell wall skeleton (CWS), preferably MPL+CWS (Detox™); and (d) a Montanide ISA;

(3) saponin adjuvants, such as Quil A or STIMULON™ QS-21 (Antigenics, Framingham, MA) (see, e.g., U.S. Pat. No. 5,057,540) may be used or particles generated therefrom such as ISCOM (immunostimulating complexes formed by the combination of cholesterol, saponin, phospholipid, and amphipathic proteins) and Iscomatrix® (having essentially the same structure as an ISCOM but without the protein);

(4) bacterial lipopolysaccharides, synthetic lipid A analogs such as aminoalkyl glucosamine phosphate compounds (AGP), or derivatives or analogs thereof, which are available from Corixa, and which are described in U.S. Pat. No. 6,113,918; one such AGP is 2-[(R)-3-tetradecanoyloxytetradecanoylamino]ethyl 2-Deoxy-4-O-phosphono-3-O-[(R)-3-tetradecanoyloxytetradecanoyl]-2-[(R)-3-tetradecanoyloxytetradecanoylamino]-b-D-glucopyranoside, which is also known as 529 (formerly known as RC529), which is formulated as an aqueous form or as a stable emulsion (5) synthetic polynucleotides such as oligonucleotides containing CpG motif(s) (U.S. Pat. No. 6,207,646);

(6) cytokines, such as interleukins (e.g., IL-1, IL-2, IL-4, IL-5, IL-6, IL-7, IL-12, IL-15, IL-18, etc.), interferons (e.g., gamma interferon), granulocyte macrophage colony stimulating factor (GM-CSF), macrophage colony stimulating factor (M-CSF), tumor necrosis factor (TNF), costimulatory molecules B7-1 and B7-2, etc; and (7) complement, such as a trimer of complement component C3d.

In another embodiment, the adjuvant is a mixture of 2, 3, or more of the above adjuvants, e.g., SBAS2 (an oil-in-water emulsion also containing 3-deacylated monophosphoryl lipid A and QS21).

Muramyl peptides include, but are not limited to, N-acetyl-muramyl-L-threonyl-D-isoglutamine (thr-MDP), N-acetyl-normuramyl-L-alanine-2-(1',2'-dipalmitoyl-sn-glycero-3-hydroxyphosphoryloxy)-ethylamine (MTP-PE), etc.

In certain embodiments, the adjuvant is an aluminum salt. The aluminum salt adjuvant may be an alum-precipitated vaccine or an alum-adsorbed vaccine. Aluminum-salt adjuvants are well known in the art and are described, for example, in Harlow, E. and D. Lane (1988; Antibodies: A Laboratory Manual Cold Spring Harbor Laboratory) and Nicklas, W. (1992; Aluminum salts. Research in Immunology 143:489-493). The aluminum salt includes, but is not limited to, hydrated alumina, alumina hydrate, alumina trihydrate (ATH), aluminum hydrate, aluminum trihydrate, Alhydrogel®, Superfos, Amphogel®, aluminum (III) hydroxide, aluminum hydroxyphosphate (Aluminum Phosphate Adjuvant (APA)), amorphous alumina, trihydrated alumina, or trihydroxyaluminum.

APA is an aqueous suspension of aluminum hydroxyphosphate. APA is manufactured by blending aluminum chloride and sodium phosphate in a 1:1 volumetric ratio to precipitate aluminum hydroxyphosphate. After the blending process, the material is size-reduced with a high-shear mixer to achieve a monodisperse particle size distribution. The product is then diafiltered against physiological saline and steam sterilized.

In certain embodiments, a commercially available Al(OH)$_3$ (e.g. Alhydrogel® or Superfos of Denmark/Accurate Chemical and Scientific Co., Westbury, NY) is used to adsorb proteins. Adsorption of protein is dependent, in another embodiment, on the pI (Isoelectric pH) of the protein and the pH of the medium. A protein with a lower pI adsorbs to the positively charged aluminum ion more strongly than a protein with a higher pI. Aluminum salts may establish a depot of Ag that is released slowly over a period of 2-3 weeks, be involved in nonspecific activation of macrophages and complement activation, and/or stimulate innate immune mechanism (possibly through stimulation of uric acid). See, e.g., Lambrecht et al., 2009, Curr Opin Immunol 21:23.

Monovalent bulk aqueous conjugates are typically blended together and diluted. Once diluted, the batch is sterile filtered. Aluminum phosphate adjuvant is added aseptically to target a final concentration of 4 µg/mL for all S. pneumoniae serotypes except serotype 6B, which is diluted to a target of 8 µg/mL, and a final aluminum concentration of 250 µg/mL. The adjuvanted, formulated batch will be filled into vials or syringes.

In certain embodiments, the adjuvant is a CpG-containing nucleotide sequence, for example, a CpG-containing oligonucleotide, in particular, a CpG-containing oligodeoxynucleotide (CpG ODN). In another embodiment, the adjuvant is ODN 1826, which may be acquired from Coley Pharmaceutical Group.

"CpG-containing nucleotide," "CpG-containing oligonucleotide," "CpG oligonucleotide," and similar terms refer to a nucleotide molecule of 6-50 nucleotides in length that contains an unmethylated CpG moiety. See, e.g., Wang et al., 2003, Vaccine 21:4297. In another embodiment, any other art-accepted definition of the terms is intended. CpG-containing oligonucleotides include modified oligonucleotides using any synthetic internucleoside linkages, modified base and/or modified sugar.

Methods for use of CpG oligonucleotides are well known in the art and are described, for example, in Sur et al., 1999, J Immunol. 162:6284-93; Verthelyi, 2006, Methods Mol Med. 127:139-58; and Yasuda et al., 2006, Crit Rev Ther Drug Carrier Syst. 23:89-110.

Administration/Dosage

The compositions and formulations described herein can be used to protect or treat a human susceptible to infection, e.g., a pneumococcal infection, by means of administering the vaccine via a systemic or mucosal route. For example, the compositions and formulations described herein can be used in a method of inducing an immune response to a S. pneumoniae capsular polysaccharide conjugate, comprising administering to a human an immunologically effective amount of an immunogenic composition or formulation described herein. In another example, the compositions and formulations described herein can be used in a method of vaccinating a human against a pneumococcal infection, comprising the step of administering to the human an immunogically effective amount of an immunogenic composition or formulation described herein.

Optimal amounts of components for a particular vaccine can be ascertained by standard studies involving observation of appropriate immune responses in subjects. For example, in another embodiment, the dosage for human vaccination is determined by extrapolation from animal studies to human data. In another embodiment, the dosage is determined empirically.

"Effective amount" of a composition of the invention refers to a dose required to elicit antibodies that significantly reduce the likelihood or severity of infectivity of a microbe, e.g., S. pneumoniae, during a subsequent challenge.

Methods using the compositions and formulations described herein can be used for the prevention and/or reduction of primary clinical syndromes caused by microbes, e.g., S. pneumoniae, including both invasive infections (meningitis, pneumonia, and bacteremia), and noninvasive infections (acute otitis media, and sinusitis).

Administration of the compositions and formulation described herein can include one or more of: injection via the intramuscular, intraperitoneal, intradermal or subcutaneous routes; or via mucosal administration to the oral/alimentary, respiratory or genitourinary tracts. In one embodiment, intranasal administration is used for the treatment of pneumonia or otitis media (as nasopharyngeal carriage of pneumococci can be more effectively prevented, thus attenuating infection at its earliest stage).

The amount of conjugate in each vaccine dose is selected as an amount that induces an immunoprotective response without significant, adverse effects. Such amount can vary depending upon the pneumococcal serotype. Generally, for polysaccharide-based conjugates, each dose will comprise 0.1 to 100 □g of each polysaccharide, particularly 0.1 to 10 □g, and more particularly 1 to 5 □g. For example, each dose can comprise 100, 150, 200, 250, 300, 400, 500, or 750 ng or 1, 1.5, 2, 3, 4, 5, 6, 7, 7.5, 8, 9, 10, 11, 12, 13, 14, 15, 16, 18, 20, 22, 25, 30, 40, 50, 60, 70, 80, 90, or 100 □g of each polysaccharide.

Optimal amounts of components for a particular vaccine can be ascertained by standard studies involving observation of appropriate immune responses in subjects. For example, in another embodiment, the dosage for human vaccination is determined by extrapolation from animal studies to human data. In another embodiment, the dosage is determined empirically.

In one embodiment, the dose of the aluminum salt is 10, 15, 20, 25, 30, 50, 70, 100, 125, 150, 200, 300, 500, or 700 □g, or 1, 1.2, 1.5, 2, 3, 5 mg or more. In yet another embodiment, the dose of aluminum salt described above is per □g of recombinant protein.

Generally, each 0.5 mL dose is formulated to contain: 2 □g of each S. pneumoniae polysaccharide, except for serotype 6B polysaccharide at 4 □g; about 32 □g CRM197 carrier protein (e.g., 32 □g±5 □g, ±3 □□g, ±2 □g, or ±1 □g); 0.125 mg of elemental aluminum (0.5 mg aluminum phosphate) adjuvant; and sodium chloride and L-histidine buffer. The sodium chloride concentration is about 150 mM (e.g., 150 mM±25 mM, ±20 mM, ±15 mM, ±10 mM, or ±5 mM) and about 20 mM (e.g., 20 mM±5 mM, ±2.5 mM, ±2 mM, ±1 mM, or ±0.5 mM) L-histidine buffer.

According to any of the methods using a composition or formulation described herein, and in one embodiment, the subject is human. In certain embodiments, the human patient is an infant (less than 1 year of age), toddler (approximately 12 to 24 months), or young child (approximately 2 to 5 years). In other embodiments, the human patient is an elderly patient (>65 years). The compositions of this invention are also suitable for use with older children, adolescents and adults (e.g., aged 18 to 45 years or 18 to 65 years).

In one embodiment of the methods using a composition or formulation described herein, a composition or formulation is administered as a single inoculation. In another embodiment, the composition or formulation is administered twice, three times or four times or more, adequately spaced apart. For example, the composition or formulation may be administered at 1, 2, 3, 4, 5, or 6 month intervals or any combination thereof. The immunization schedule can follow that designated for pneumococcal vaccines. For example, the routine schedule for infants and toddlers against invasive disease caused by S. pneumoniae is 2, 4, 6 and 12-15 months of age. Thus, in a preferred embodiment, the composition is administered as a 4-dose series at 2, 4, 6, and 12-15 months of age.

The compositions described herein may also include one or more proteins from S. pneumoniae. Examples of S. pneumoniae proteins suitable for inclusion include those identified in International Patent Application Publication Nos. WO 02/083855 and WO 02/053761.

Formulations

The compositions described herein can be administered to a subject by one or more method known to a person skilled in the art, such as parenterally, transmucosally, transdermally, intramuscularly, intravenously, intra-dermally, intranasally, subcutaneously, intra-peritonealy, and formulated accordingly.

In one embodiment, compositions described herein are administered via epidermal injection, intramuscular injection, intravenous, intra-arterial, subcutaneous injection, or intra-respiratory mucosal injection of a liquid preparation. Liquid formulations for injection include solutions and the like.

The composition can be formulated as single dose vials, multi-dose vials or as pre-filled syringes.

In another embodiment, compositions are administered orally, and are thus formulated in a form suitable for oral administration, i.e., as a solid or a liquid preparation. Solid oral formulations include tablets, capsules, pills, granules, pellets and the like. Liquid oral formulations include solutions, suspensions, dispersions, emulsions, oils and the like.

Pharmaceutically acceptable carriers for liquid formulations are aqueous or nonaqueous solutions, suspensions, emulsions or oils. Examples of nonaqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs.

The pharmaceutical composition may be isotonic, hypotonic or hypertonic. However, it is often preferred that a pharmaceutical composition for infusion or injection is essentially isotonic when it is administered. Hence, for storage the pharmaceutical composition may preferably be isotonic or hypertonic. If the pharmaceutical composition is hypertonic for storage, it may be diluted to become an isotonic solution prior to administration.

The isotonic agent may be an ionic isotonic agent such as a salt or a non-ionic isotonic agent such as a carbohydrate. Examples of ionic isotonic agents include but are not limited to NaCl, $CaCl_2$, KCl and $MgCl_2$. Examples of non-ionic isotonic agents include but are not limited to sucrose, trehalose, mannitol, sorbitol and glycerol.

It is also preferred that at least one pharmaceutically acceptable additive is a buffer. For some purposes, for example, when the pharmaceutical composition is meant for infusion or injection, it is often desirable that the composition comprises a buffer, which is capable of buffering a solution to a pH in the range of 4 to 10, such as 5 to 9, for example 6 to 8.

The buffer may for example be selected from the group consisting of Tris, acetate, glutamate, lactate, maleate, tartrate, phosphate, citrate, carbonate, glycinate, L-histidine, glycine, succinate and triethanolamine buffer.

The buffer may furthermore for example be selected from USP compatible buffers for parenteral use, in particular, when the pharmaceutical formulation is for parenteral use. For example the buffer may be selected from the group consisting of monobasic acids such as acetic, benzoic, gluconic, glyceric and lactic; dibasic acids such as aconitic, adipic, ascorbic, carbonic, glutamic, malic, succinic and tartaric, polybasic acids such as citric and phosphoric; and bases such as ammonia, diethanolamine, glycine, triethanolamine, and Tris.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, glycols such as propylene glycols or polyethylene glycol, Polysorbate 80 (PS-80), Polysorbate 20 (PS-20), and Poloxamer 188 (P188) are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

The formulations may also contain a surfactant. Preferred surfactants include, but are not limited to: the polyoxyethylene sorbitan esters surfactants (commonly referred to as the Tweens), especially PS-20 and PS-80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. A preferred surfactant for including in the emulsion is PS-20 or PS-80.

Mixtures of surfactants can be used, e.g. PS-80/Span 85 mixtures. A combination of a polyoxyethylene sorbitan ester such as polyoxyethylene sorbitan monooleate (PS-80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants are: polyoxyethylene sorbitan esters (such as PS-80) 0.01 to 1% w/v, in particular about 0.1% w/v; octyl- or nonylphenoxy polyoxyethanols (such as Triton X-100, or other detergents in the Triton series) 0.001 to 0.1% w/v, in particular 0.005 to 0.02% w/v; polyoxyethylene ethers (such as laureth 9) 0.1 to 20% w/v, preferably 0.1 to 10% w/v and in particular 0.1 to 1% w/v or about 0.5% w/v.

In certain embodiments, the composition consists essentially of L-histidine (20 mM), saline (150 mM) and 0.2% w/v PS-20 at a pH of 5.8 with 250 □g/mL of APA (Aluminum Phosphate Adjuvant). PS-20 can range from 0.005 to 0.1% w/v with the presence of PS-20 or PS-80 in formulation controlling aggregation during simulated manufacture and in shipping using primary packaging. Process consists of combining blend of up to 44 S. pneumoniae polysaccharide serotypes in L-histidine, sodium chloride, and PS-20 then combining this blended material with APA and sodium chloride with or without antimicrobial preservatives.

The choice of surfactant may need to be optimized for different drug products and drug substances. For multivalent vaccines containing 15 or more S. pneumoniae polysaccharide serotypes, PS-20 and P188 are preferred. The choice of chemistry used to prepare the conjugate can also influence the stabilization of the formulation. In particular, as exemplified below, pneumococcal polysaccharide-protein conjugates prepared in aqueous or DMSO solvent and combined in a multivalent composition show significant differences in stability depending on the particular surfactant systems used for formulation.

For the formulations described herein, a poloxamer generally has a molecular weight in the range from 1,100 Da to 17,400 Da, from 7,500 Da to 15,000 Da, or from 7,500 Da to 10,000 Da. The poloxamer can be selected from poloxamer 188 or poloxamer 407. The final concentration of the poloxamer in the formulations of the invention is from 0.001 to 5% w/v, or 0.025 to 1% w/v. A surfactant system comprising a poloxamer must further comprise a polyol. In certain aspects, the polyol is propylene glycol and is at final concentration from 1 to 20% w/v. In certain aspects, the polyol is polyethylene glycol 400 and is at final concentration from 1 to 20% w/v.

Suitable polyols for the formulations are polymeric polyols, particularly polyether diols including, but are not limited to, propylene glycol and polyethylene glycol, Polyethylene glycol monomethyl ethers. Propylene glycol is available in a range of molecular weights of the monomer from ~425 Da to ~2,700 Da. Polyethylene glycol and Polyethylene glycol monomethyl ether is also available in a range of molecular weights ranging from ~200 Da to ~35,000 Da including but not limited to PEG200, PEG300, PEG400, PEG1000, PEG MME 550, PEG MME 600, PEG MME 2000, PEG MME 3350 and PEG MME 4000. A preferred polyethylene glycol is polyethylene glycol 400. The final concentration of the polyol in the formulations may be 1 to 20% w/v or 6 to 20% w/v.

The formulation also contains a pH-buffered saline solution. The buffer may, for example, be selected from the group consisting of Tris, acetate, glutamate, lactate, maleate, tartrate, phosphate, citrate, carbonate, glycinate, L-histidine, glycine, succinate, HEPES (4-(2-hydroxyethyl)-1-piperazineethanesulfonic acid), MOPS (3-(N-morpholino)propanesulfonic acid), MES (2-(N-morpholino)ethanesulfonic acid) and triethanolamine buffer. The buffer is capable of buffering a solution to a pH in the range of 4 to 10, 5.2 to 7.5, or 5.8 to 7.0. In certain aspects, the buffer selected from the group consisting of phosphate, succinate, L-histidine, MES, MOPS, HEPES, acetate or citrate. The buffer may furthermore, for example, be selected from USP compatible buffers for parenteral use, in particular, when the pharmaceutical formulation is for parenteral use. The concentrations of buffer will range from 1 mM to 50 mM or 5 mM to 50 mM. In certain aspects, the buffer is L-histidine at a final concentration of 5 mM to 50 mM, or succinate at a final concentration of 1 mM to 10 mM. In certain aspects, the L-histidine is at a final concentration of 20 mM±2 mM.

While the saline solution (i.e., a solution containing NaCl) is preferred, other salts suitable for formulation include but are not limited to, $CaCl_2$, KCl and $MgCl_2$ and combinations thereof. Non-ionic isotonic agents including but not limited to sucrose, trehalose, mannitol, sorbitol and glycerol may be used in lieu of a salt. Suitable salt ranges include, but not are limited to 25 mM to 500 mM or 40 mM to 170 mM. In one aspect, the saline is NaCl, optionally present at a concentration from 20 mM to 170 mM.

In a preferred embodiment, the formulations comprise a L-histidine buffer with sodium chloride.

In another embodiment, the pharmaceutical composition is delivered in a controlled release system. For example, the agent can be administered using intravenous infusion, a transdermal patch, liposomes, or other modes of administration. In another embodiment, polymeric materials are used; e.g. in microspheres in or an implant.

The compositions described herein may also include one or more proteins from *S. pneumoniae*. Examples of *S. pneumoniae* proteins suitable for inclusion include those identified in International Patent Application Publication Nos. WO 02/083855 and WO 02/053761.

Analytical Methods
Molecular Weight and Concentration Analysis of Conjugates Using HPSEC/UV/MALS/RI Assay Conjugate samples are injected and separated by high performance size-exclusion chromatography (HPSEC). Detection is accomplished with ultraviolet (UV), multi-angle light scattering (MALS) and refractive index (RI) detectors in series. Protein concentration is calculated from UV280 using an extinction coefficient. Polysaccharide concentration is deconvoluted from the RI signal (contributed by both protein and polysaccharide) using the dn/dc factors which are the change in a solution's refractive index with a change in the solute concentration reported in mL/g. Average molecular weight of the samples are calculated by Astra software (Wyatt Technology Corporation, Santa Barbara, CA) using the measured concentration and light scattering information across the entire sample peak. There are multiple forms of average values of molecular weight for polydispersed molecules. For example, number-average molecular weight Mn, weight-average molecular weight Mw, and z-average molecular weight Mz (Molecules, 2015, 20:10313-10341). Unless specified, the term "molecular weight", as used throughout the specification, is the weight-average molecular weight.

Determination of Lysine Consumption in Conjugated Protein as a Measure of the Number of Covalent Attachments Between Polysaccharide and Carrier Protein The Waters AccQ-Tag amino acid analysis (AAA) is used to measure the extent of conjugation in conjugate samples. Samples are hydrolyzed using vapor phase acid hydrolysis in the Eldex workstation, to break the carrier proteins down into their component amino acids. The free amino acids are derivatized using 6-aminoquinolyl-N-hydroxysuccinimidyl carbamate (AQC). The derivatized samples are then analyzed using UPLC with UV detection on a C18 column. The average protein concentration is obtained using representative amino acids other than lysine. Lysine consumption during conjugation (i.e., lysine loss) is determined by the difference between the average measured amount of lysine in the conjugate and the expected amount of lysine in the starting protein.

Free Polysaccharide Testing

Free polysaccharide (i.e., polysaccharide that is not conjugated with CRM197) in the conjugate sample is measured by first precipitating free protein and conjugates with deoxycholate (DOC) and hydrochloric acid. Precipitates are then filtered out and the filtrates are analyzed for free polysaccharide concentration by HPSEC/UV/MALS/RI. Free polysaccharide is calculated as a percentage of total polysaccharide measured by HPSEC/UV/MALS/RI.

Free Protein Testing

Free polysaccharide, polysaccharide-CRM197 conjugate, and free CRM197 in the conjugate samples are separated by capillary electrophoresis in micellar electrokinetic chromatography (MEKC) mode. Briefly, samples are mixed with MEKC running buffer containing 25 mM borate, 100 mM SDS, pH 9.3, and are separated in a preconditioned bare-fused silica capillary. Separation is monitored at 200 nm and free CRM197 is quantified with a CRM197 standard curve. Free protein results are reported as a percentage of total protein content determined by the HPSEC/UV/MALS/RI procedure.

Having described various embodiments of the invention with reference to the accompanying description and drawings, it is to be understood that the invention is not limited to those precise embodiments, and that various changes and modifications may be effected therein by one skilled in the art without departing from the scope or spirit of the invention as defined in the appended claims.

The following examples illustrate, but do not limit the invention.

EXAMPLES

Example 1: Preparation of *S. pneumoniae* Capsular Polysaccharides

Methods of culturing pneumococci are well known in the art. See, e.g., Chase, 1967, Methods of Immunology and Immunochemistry 1:52. Methods of preparing pneumococcal capsular polysaccharides are also well known in the art. See, e.g., European Patent No. EP 0 497 524 B 1. The process described below generally follows the method described in European Patent No. EP 0 497 524 B1 and is generally applicable to all pneumococcal serotypes except where specifically modified.

Isolates of pneumococcal serotypes 3, 8, 12F were obtained from University of Pennsylvania (Dr. Robert Austrian). Isolates of pneumococcal serotypes 15A, 16F, 23A, 24F, 35B were obtained from the Merck Culture Collection. Isolates of pneumococcal serotype 23B and 31 were obtained from Centers for Disease Control and Prevention (Atlanta, GA). Isolate of pneumococcal serotype 17F was obtained from the FDA Office of Biologics (Dr. John Robbins). Isolate of pneumococcal serotype 20 was obtained from ATCC. Where needed, subtypes can be differentiated on the basis of Quelling reaction using specific antisera. See, e.g., U.S. Pat. No. 5,847,112. The obtained isolates were further clonally isolated by plating serially in two stages on agar plates consisting of an animal-component free medium containing soy peptone, yeast extract, and glucose without hemin. Clonal isolates for each serotype were further expanded in liquid culture using animal-component free media containing soy peptone, yeast extract, HEPES, sodium chloride, sodium bicarbonate, potassium phosphate, glucose, and glycerol to prepare the pre-master cell banks.

The production of each serotype of pneumococcal polysaccharide consisted of a cell expansion and batch production fermentation followed by chemical inactivation prior to downstream purification. A thawed cell bank vial from each serotype was expanded using a shake flask or culture bottle containing a pre-sterilized animal-component free growth media containing soy peptone or soy peptone ultrafiltrate, yeast extract or yeast extract ultrafiltrate, HEPES, sodium chloride, sodium bicarbonate, potassium phosphate, and glucose. The cell expansion culture was grown in a sealed shake flask or bottle to minimize gas exchange with temperature and agitation control. After achieving a specified culture density, as measured by optical density at 600 nm, a portion of the cell expansion culture was transferred to a production fermentor containing pre-sterilized animal-component free growth media containing soy peptone or soy peptone ultrafiltrate, yeast extract or yeast extract ultrafiltrate, sodium chloride, potassium phosphate, and glucose. Temperature, pH, pressure, and agitation were controlled. Airflow overlay was also controlled as sparging was not used.

The batch fermentation was terminated via the addition of a chemical inactivating agent, phenol, when glucose was nearly exhausted. Pure phenol was added to a final concentration of 0.8-1.2% to inactivate the cells and liberate the capsular polysaccharide from the cell wall. Primary inactivation occurs for a specified time within the fermentor where temperature and agitation continue are to be controlled. After primary inactivation, the batch was transferred to another vessel where it was held for an additional specified time at controlled temperature and agitation for complete inactivation. This was confirmed by either microbial plating techniques or by verification of the phenol concentration and specified time. The inactivated broth was then purified.

Purification of Ps

The purification of the pneumococcal polysaccharide consisted of several centrifugation, depth filtration, concentration/diafiltration operations, and precipitation steps. All procedures were performed at room temperature unless otherwise specified.

Inactivated broth from the fermentor cultures of *S. pneumoniae* were flocculated with a cationic polymer (such as BPA-1000, Petrolite "Tretolite" and "Spectrum 8160" and poly(ethyleneimine), "Millipore pDADMAC"). The cationic polymers bound to the impurity protein, nucleic acids and cell debris. Following the flocculation step and an aging period, flocculated solids were removed via centrifugation and multiple depth filtration steps. Clarified broth was concentrated and diafiltered using a 100 kDa to 500 kDa MWCO (molecular weight cutoff) filter. Diafiltration was accomplished using Tris, $MgCl_2$ buffer and sodium phosphate buffer. Diafiltration removed residual nucleic acid and protein.

Further impurities removal was accomplished by reprecipitation of the polysaccharide in sodium acetate and phenol with denatured alcohol and/or isopropanol. During the phenol precipitation step, sodium acetate in sodium phosphate saline buffer and phenol (liquefied phenols or solid phenols) was charged to the diafiltered retentate. Alcohol fractionation of the polysaccharide was then conducted in two stages. In the first stage a low percent alcohol was added to the preparation to precipitate cellular debris and other unwanted impurities, while the crude polysaccharide remained in solution. The impurities were removed via a depth filtration step. The polysaccharide was then recovered from the solution by adding additional isopropanol or denatured alcohol to the batch. The precipitated polysaccharide pellet was recovered by centrifugation, triturated and dried as a powder and stored frozen at −70° C.

Example 2: General Conjugation Methods

Polysaccharide Size Reduction and Oxidation

Purified pneumococcal capsular polysaccharide powder was dissolved in water and 0.45-micron filtered. Unless otherwise specified, polysaccharides were homogenized to reduce the polysaccharide molecular mass. Homogenization pressure and number of passes through the homogenizer were controlled to serotype-specific targets (150-1000 bar; 4-7 passes).

Size-reduced polysaccharide was 0.2 micron filtered and then concentrated and diafiltered against distilled water using a 5 kDa or 10 kDa NMWCO tangential flow ultrafiltration membrane.

The polysaccharide solution was then adjusted to 22° C. and pH 5 with a sodium acetate buffer to minimize polysaccharide size reduction due to activation.

The purified polysaccharides were prepared for conjugation, i.e., activated, using sodium metaperiodate oxidation (See Anderson et al., 1986, *J. Immunol.* 137:1181-1186; and U.S. Patent Application Publication No. US20110195086). A 100 mM sodium metaperiodate solution was added to the polysaccharide solution in 50 mM sodium acetate. The amount of sodium metaperiodate added was serotype-specific, ranging from approximately 0.1 to 0.5 moles of sodium metaperiodate per mole of polysaccharide repeating unit, to achieve a target level of polysaccharide activation (moles aldehyde per mole of polysaccharide repeating unit). The sample was mixed for a target incubation time protected from light.

The activated product was diafiltered against 10 mM potassium phosphate, pH 6.4 followed by distilled water using a 5 kDa or 10 kDa NMWCO tangential flow ultrafiltration membrane, followed by additional diafiltration against water. Ultrafiltration for all serotypes was conducted at 2-8° C.

Conjugation

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharides were formulated for lyophilization at 1-6 mg Ps/mL with sucrose concentration of 0.5-30% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a target polysaccharide concentration and a polysaccharide to CRM197 mass ratio. The mass ratio was selected to control the polysaccharide to CRM197 ratio in the resulting conjugate. Sodium cyanoborohydride (1 mole per mole of polysaccharide repeating unit) was added, and conjugation proceeded for a target incubation time at 22° C.

Reduction with Sodium Borohydride

Sodium borohydride (2 mole per mole of polysaccharide repeating unit) was added following the conjugation reaction. The batch was diluted into 150 mM sodium chloride with approximately 0.025% (w/v) polysorbate 20, at approximately 4° C. Potassium phosphate buffer was then added to neutralize the pH.

Final Filtration and Product Storage

Conjugates were then dialyzed against 150 mM sodium chloride with 0.05% (w/v) polysorbate 20 at approximately 4° C. using a 300 kDa NMWC membrane, or diafiltered against 150 mM sodium chloride, with or without 25 mM potassium phosphate pH 7 using a 30 kDa NMWC tangential flow ultrafiltration membrane, followed by concentration and diafiltration against 10 mM histidine in 150 mM sodium chloride, pH 7.0, with 0.015% (w/v) polysorbate 20, at 4° C. using a 300 kDa NMWCO tangential flow ultrafiltration membrane. The retentate batch was diluted with additional 10 mM histidine in 150 mM sodium chloride, pH 7.0 and 0.2 micron filtered. The final conjugate solution was dispensed into aliquots and frozen at ≤−60° C.

Example 3: Acid Hydrolysis of Polysaccharides from Serotypes 12F, 23A, 24F, and 31

Conjugation of pneumococcal polysaccharides to proteins by reductive amination in an aprotic solvent such as DMSO has been previously described. Activated polysaccharides (Ps) and proteins (Pr) are typically lyophilized, resuspended in DMSO, then blended and incubated with sodium cyanoborohydride and sodium borohydride to achieve conjugation. Polysaccharides may be mechanically size-reduced (e.g. by homogenization) prior to oxidation to reduce the Ps molecular mass and provide a consistent Ps size for conjugation. For many pneumococcal serotypes, conjugation of mechanically size-reduced and oxidized Ps yields conjugates that meet target attributes for size, lysine consumption, free polysaccharide, and free protein. However for some serotypes it was found that target conjugate attributes were difficult to achieve with this process, even after optimizing process parameters.

Ps Size Reduction

Purified pneumococcal capsular polysaccharide powder from serotypes 23A, 24F, and 31 were dissolved in water. Different experimental arms were processed either mechanically by homogenization or chemically by acid hydrolysis to reduce the molecular mass of the Ps. Homogenization pressure and number of passes through the homogenizer were controlled to serotype-specific targets (150-1000 bar; 4-7 passes). Acid hydrolysis was performed by heating the batch to 90-92° C., adding concentrated acetic acid to a final concentration of 200 mM, then incubating for up to 90 minutes. At the end of the incubation period, the batch was neutralized by adding concentrated potassium phosphate pH 7 buffer to a final concentration of 400 mM and cooling to ≤22° C. Size-reduced polysaccharide was 0.2-micron filtered and then concentrated and diafiltered against water using a 5 kDa or 10 kDa NMWC tangential flow ultrafiltration membrane.

The polysaccharides were conjugated as described in Example 2.

Experimental conditions and results are summarized in Table 1.

TABLE 1

Summary of experimental arms, Ps size-reduction by homogenization vs acid hydrolysis, for S. pneumoniae serotypes 23A, 24F, and 31

| Serotype | Size Reduction Method | Size Reduction Conditions | NaIO₄ Charge (MEq) | Oxidized Ps Mw (kD) | Conjugation Conditions, [Ps] (mg/mL)/Ps:Pr/ Time (hrs) / [NaCl] (mM) | Conjugate Mw (kD) | Conjugate Lys Loss (mol/mol) | Conjugate Free Ps/ Free Pr Fraction |
|---|---|---|---|---|---|---|---|---|
| 23A | Homogenized | 600 bar/ 3 passes | 0.20 | 319 | 3/1.5/3/25 | 6774 | 8.4 | 7%/ 18% |
|  | Acid Hydrolysis | 90° C./ 90 min | 0.20 | 97 | 3/1.5/2/25 | 2996 | 12.6 | 11%/ <3% |
| 24F | Homogenized | 600 bar/ 5 passes | 0.18 | 227 | 2/1.5/17/ 25 | 8727 | 10.6 | 51%/ 15% |
|  | Acid Hydrolysis | 92° C./ 90 min | 0.18 | 100 | 2/1.5/15/25 | 5816 | 9.0 | 22%/ 2% |
| 31 | Homogenized | 400 bar/ 5 passes | 0.12 | 186 | 4/1.5/4/25 | 3323 | 11.5 | 18%/ 3% |
|  | Acid hydrolysis | 90° C./ 30 min | 0.16 | 119 | 4/.2/4/25 | 3201 | 13.3 | 2%/ <2% |

As seen in Table 1, size reduction by acid hydrolysis provided a means to achieve higher lysine loss (serotype 23A), lower free Ps (serotype 24F and 31), or lower free Pr (serotypes 23A, 24F and 31) compared to homogenization. For serotypes 23A and 24F, the higher free protein levels for homogenization may have been associated with aggregated forms which may in turn have contributed to the higher measured conjugate Mw levels.

Without being bound by any particular theory, the data suggest that the lower molecular weight of oxidized polysaccharide (preferentially less than 150 KDa) achieved through acid hydrolysis helped to improve the conjugation (less free Ps or free Pr). It is believed that alternative size reduction processes (e.g., through acid hydrolysis) may be used to achieve polysaccharide at this preferred size range to achieve similar conjugation benefits.

Impact of Acid Type while Maintaining Constant pH on Acid Hydrolysis of Serotype 12F To determine whether the acid type had an impact on polysaccharide size, acid hydrolysis using hydrochloric acid was compared to acetic acid. Purified pneumococcal capsular polysaccharide powder from S. pneumoniae serotype 12F was dissolved in water and 0.45 μm filtered. The batch was diluted to 2.5 g Ps/L and split into two arms. Acid hydrolysis was performed on both arms by first heating them to 80° C. Acid was added to maintain similar pH across both arms. To one arm, glacial acetic acid was added to a final concentration of 200 mM, pH 2.6. To the other arm, 1N hydrochloric acid was added to a final concentration of 2.5 mM, pH 2.7. Both arms were then incubated for 155 minutes. At the end of the incubation period, the arms were neutralized by adding concentrated potassium phosphate pH 7 buffer to a final concentration of approximately 400 mM and cooling to 4° C. The results are shown in Table 2.

TABLE 2

Acid hydrolysis of *S. pneumoniae* 12F polysaccharide using hydrochloric acid

| Description | Acid hydrolysis temp (° C.) | Acid hydrolysis time (min) | Acid hydrolysis pH | Mn (kD) | Mw (kD) | Polydispersity | Ps Conc (mg/mL) |
|---|---|---|---|---|---|---|---|
| Acid hydrolysis feed | N/A | N/A | N/A | 349.7 | 448.6 | 1.283 | 2.496 |
| Acid hydrolyzed with 200 mM acetic acid | 80.0 +/− 0.5 | 155 | 2.64 | 75.2 | 104.4 | 1.388 | 1.866 |
| Acid hydrolyzed with 2.5 mM hydrochloric acid | 80.0 +/− 0.5 | 155 | 2.70 | 76.5 | 106.6 | 1.393 | 1.856 |

Both acid hydrolysis conditions produced similar sized polysaccharides.

Example 4: Impact of Sucrose to Polysaccharide Mass Ratio on Dissolution of Polysaccharides from *S. pneumoniae* Serotypes 3, 8 and 24F in DMSO In preparation for conjugation of polysaccharides to proteins in an aprotic solvent, polysaccharide and protein solutions are typically lyophilized. For most pneumococcal serotypes, formulating activated polysaccharides (Ps) for lyophilization in aqueous solution at 6 mg Ps/mL with sucrose concentration of 5% w/v (50 mg sucrose/mL) resulted in lyophilized material suitable for redissolution in DMSO and conjugation. For serotypes 3, 8, and 24F, it was discovered that this formulation (6 mg Ps/mL, 50 mg sucrose/mL, sucrose:Ps mass ratio=8.3) yielded lyophilized material that did not dissolve in DMSO.

Experiments were performed to optimize the activated polysaccharide lyophilization formulation for dissolution in DMSO. Activated polysaccharides were formulated across a range of polysaccharide concentrations (1-6 mg Ps/mL) and sucrose concentrations (50-300 mg sucrose/mL) in polypropylene containers. Solutions were lyophilized to remove water, then DMSO was added at ambient temperature with mixing to redissolve polysaccharides. Successful dissolution was determined by visual observation.

Results for serotype 3, 24F, and 8 are shown in Tables 3, 4, and 5 respectively.

TABLE 3

Serotype 3 Lyophilization Formulation and Dissolution Experiments

| | | Pre-lyo formulation conditions | | | Post-lyo addition of DMSO | |
|---|---|---|---|---|---|---|
| Experimental Condition | Polysaccharide Mw (kD) | [Ps], (mg/mL) | [sucrose], (mg/mL) | Sucrose:Ps mass ratio | [Ps], mg/mL | Dissolution |
| 1 | 211 | 6.0 | 30 | 5.0 | 2.0 | No |
| 2 | 211 | 6.0 | 40 | 6.7 | 4.0 | No |
| 3 | 211 | 6.0 | 50 | 8.3 | 6.0 | No |
| 4 | 212 | 1.0 | 5.0 | 5.0 | 2.0 | No |
| 5 | 212 | 1.0 | 10 | 10 | 2.0 | No |
| 6 | 212 | 1.0 | 20 | 20 | 2.0 | No |
| 7 | 212 | 1.0 | 50 | 50 | 2.0 | Yes |
| 8 | 212 | 1.0 | 100 | 100 | 2.0 | Yes |
| 9 | 212 | 6.0 | 50 | 8.3 | 6.0 | No |
| 10 | 212 | 4.0 | 200 | 50 | 6.0 | Yes |
| 11 | 212 | 3.0 | 150 | 50 | 6.0 | Yes |
| 12 | 212 | 2.0 | 100 | 50 | 6.0 | Yes |
| 13 | 212 | 4.0 | 200 | 50 | 3.0 | Yes |
| 14 | 257 | 2.0 | 100 | 50 | 2.0-5.0 (multiple arms) | Yes (all arms) |
| 15 | 253 | 2.0 | 40 | 20 | 3.0 | No |
| 16 | 253 | 2.0 | 60 | 30 | 3.0 | Yes |
| 17 | 253 | 2.0 | 80 | 40 | 3.0 | Yes |

TABLE 3-continued

Serotype 3 Lyophilization Formulation and Dissolution Experiments

| | | Pre-lyo formulation conditions | | | Post-lyo addition of DMSO | |
|---|---|---|---|---|---|---|
| Experimental Condition | Polysaccharide Mw (kD) | [Ps], (mg/mL) | [sucrose], (mg/mL) | Sucrose:Ps mass ratio | [Ps], mg/mL | Dissolution |
| 18 | 253 | 2.0 | 100 | 50 | 3.0 | Yes |
| 19 | 253 | 4.0 | 80 | 20 | 3.0 | No |
| 20 | 253 | 4.0 | 120 | 30 | 3.0 | Not fully dissolved |
| 21 | 253 | 4.0 | 160 | 40 | 3.0 | Yes |
| 22 | 253 | 4.0 | 200 | 50 | 3.0 | Yes |

TABLE 4

Serotype 24F Lyophilization Formulation and Dissolution Experiments

| | | Pre-lyo formulation conditions | | | Post-lyo addition of DMSO | |
|---|---|---|---|---|---|---|
| Experimental Condition | Polysaccharide Mw (kD) | [Ps], (mg/mL) | [sucrose], (mg/mL) | Sucrose:Ps mass ratio | [Ps], mg/mL | Dissolution |
| 1 | 142 | 6 | 50 | 8.3 | 2.0-8.0 (multiple arms) | No |
| 2 | 142 | 6 | 50 | 8.3 | 4.0 | No |
| 3 | 142 | 6 | 300 | 50 | 6.0 | Yes |
| 4 | 142 | 4 | 200 | 50 | 4.0 | Yes* |
| 5 | 142 | 3 | 150 | 50 | 4.0 | Yes |
| 6 | 142 | 2 | 100 | 50 | 4.0 | Yes |
| 7 | 142 | 2 | 100 | 50 | 4.0-8.0 (multiple arms) | Yes |
| 8 | 132 | 6 | 50 | 8.3 | 4.0-8.0 (multiple arms) | No |
| 9 | 132 | 2 | 100 | 50 | 4.0-8.0 (multiple arms) | Yes |
| 10 | 142 | 2 | 100 | 50 | 3.0-4.0 (multiple arms) | Yes |
| 11 | 227 | 2 | 100 | 50 | 2.0-6.0 (multiple arms) | Yes |
| 12 | 63 | 6 | 50 | 8.3 | 3.0-4.0 (multiple arms) | No |
| 13 | 63 | 2 | 100 | 50 | 3.0-5.0 (multiple arms) | Yes |

*In Experimental condition 4, a single small visible particle was observed that it is not believed to be due to incomplete dissolution

TABLE 5

Serotype 8 Lyophilization Formulation and Dissolution Experiments

| | | Pre-lyo formulation conditions | | | Post-lyo addition of DMSO | |
|---|---|---|---|---|---|---|
| Experimental Condition | Polysaccharide Mw (kD) | [Ps], (mg/mL) | [sucrose] (mg/mL) | Sucrose:Ps mass ratio | [Ps], mg/mL | Dissolution |
| 1 | 233 | 6.0 | 50 | 8.3 | 4.0-8.0 (multiple arms) | No |

TABLE 5-continued

Serotype 8 Lyophilization Formulation and Dissolution Experiments

| Experimental Condition | Polysaccharide Mw (kD) | Pre-lyo formulation conditions | | | Post-lyo addition of DMSO | |
|---|---|---|---|---|---|---|
| | | [Ps] (mg/mL) | [sucrose] (mg/mL) | Sucrose:Ps mass ratio | [Ps], mg/mL | Dissolution |
| 2 | 233 | 2.0 | 100 | 50 | 4.0-8.0 (multiple arms) | Yes |
| 3 | 252 | 2.0 | 100 | 50 | 4.0-8.0 (multiple arms) | Yes |

For these serotypes, full dissolution was observed across the range of polysaccharide concentrations studied (for both lyophilization and dissolution), however dissolution was dependent on both the polysaccharide and sucrose concentrations. Specifically, when the mass ratio of sucrose was less than 30× that of the polysaccharide, dissolution in DMSO following lyophilization was not achieved. The most consistent dissolution results were found when the sucrose mass ratio was at least 40× that of the polysaccharide.

Several arms from the positive dissolution conditions were successfully conjugated to CRM197 as described in Example 2.

Impact of Sugar Type and Sugar to Polysaccharide Mass Ratio on Dissolution of S. pneumoniae Polysaccharide from Serotype 3 in DMSO Experiments were performed to assess the impact of sugar type and sugar:polysaccharide mass ratio on lyophilized activated polysaccharide dissolution in DMSO. Activated serotype 3 polysaccharide was formulated at either 2.5 or 6 mg Ps/mL and at a range of sugar concentrations (50-150 mg sugar/mL) in polypropylene containers. Sugars tested were sucrose, trehalose and mannitol. Solutions were lyophilized to remove water then DMSO was added at ambient temperature with mixing to redissolve polysaccharides. Successful dissolution was determined by visual observation. The results are shown in Table 6.

TABLE 6

Impact of Sugar Type on Serotype 3 Polysaccharide

| Experimental Condition | Polysaccharide Mw (kD) | Pre-lyo formulation conditions | | | | Post-lyo addition of DMSO | |
|---|---|---|---|---|---|---|---|
| | | [Ps] (mg/mL) | Sugar Type | [Sugar] (mg/mL) | Sugar:Ps mass ratio | [Ps], mg/mL | Dissolution |
| A1 | 171 | 6.0 | Sucrose | 50 | 8.3 | 4.4 | No |
| A2 | 171 | 2.5 | Sucrose | 50 | 20 | 4.4 | No |
| A3 | 171 | 2.5 | Sucrose | 75 | 30 | 4.4 | Yes |
| A4 | 171 | 2.5 | Sucrose | 100 | 40 | 4.4 | Yes |
| A5 | 171 | 2.5 | Sucrose | 125 | 50 | 4.4 | Yes |
| A6 | 171 | 2.5 | Sucrose | 150 | 60 | 4.4 | Yes |
| B1 | 171 | 6.0 | Trehalose | 50 | 8.3 | 4.4 | No |
| B2 | 171 | 2.5 | Trehalose | 50 | 20 | 4.4 | No |
| B3 | 171 | 2.5 | Trehalose | 75 | 30 | 4.4 | Yes |
| B4 | 171 | 2.5 | Trehalose | 100 | 40 | 4.4 | Yes |
| B5 | 171 | 2.5 | Trehalose | 125 | 50 | 4.4 | Yes |
| B6 | 171 | 2.5 | Trehalose | 150 | 60 | 4.4 | Yes |
| C1 | 171 | 6.0 | Mannitol | 50 | 8.3 | 4.4 | No |
| C2 | 171 | 2.5 | Mannitol | 50 | 20 | 4.4 | No |
| C3 | 171 | 2.5 | Mannitol | 75 | 30 | 4.4 | Yes* |
| C4 | 171 | 2.5 | Mannitol | 100 | 40 | 4.4 | Yes |
| C5 | 171 | 2.5 | Mannitol | 125 | 50 | 4.4 | Yes |
| C6 | 171 | 2.5 | Mannitol | 150 | 60 | 4.4 | No |

*viscous

For all sugars used, dissolution in DMSO was achieved for sugar mass ratios of 30× and higher with the exception of mannitol, which appeared to reach the solubility limit in DMSO at 60×. The most consistent dissolution results were found when the sugar mass ratio was at least 40× that of the polysaccharide.

Another experiment was performed looking at using combinations of sugars in activated serotype 3 polysaccharide lyophilization formulations. All arms were formulated to a total sugar mass ratio at 40× since this ratio yielded consistent dissolution in DMSO. The molecular weight of the polysaccharide was 171 kD. All arms used sucrose, either alone, with trehalose or with mannitol. Solutions were lyophilized to remove water then DMSO was added at ambient temperature with mixing to redissolve polysaccharides. Successful dissolution was determined by visual observation. The results are shown in Table 7.

TABLE 7

Sugar combinations for dissolation of polysaccharides in DMSO

| | Pre-lyo formulation conditions | | | | | Total | Post-lyo addition of DMSO | |
|---|---|---|---|---|---|---|---|---|
| | Sucrose:Ps | | | Sugar 2:Ps | | Sugar:Ps | | |
| [Ps], (mg/mL) | [Sucrose] [(mg/mL)] | mass ratio | Sugar 2 Type | [Sugar 2] (mg/mL) | mass ratio | mass ratio | [Ps], mg/mL | Dissolution |
| 2.5 | 100 | 40 | N/A | 0 | 0 | 40 | 4.4 | Yes |
| 2.5 | 75 | 30 | Trehalose | 25 | 10 | 40 | 4.4 | Yes |
| 2.5 | 50 | 20 | Trehalose | 50 | 20 | 40 | 4.4 | Yes |
| 2.5 | 75 | 30 | Mannitol | 25 | 10 | 40 | 4.4 | Yes |

Dissolution in DMSO was achieved for all arms tested.

Example 5: Effect of Sodium Chloride on Conjugation of S. pneumoniae Serotypes 15A, 16F, 17F, 20, 24F, and 35B Using Reductive Amination in DMSO Activated polysaccharides were formulated for lyophilization at 2-6 mg Ps/mL with sucrose concentrations of 5-10% w/v in polypropylene containers. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved in DMSO. For some arms, a 5 M stock solution of sodium chloride was used to spike the CRM197 solution prior to lyophilization or the redissolved Ps solution to achieve final concentrations during conjugation of 10-100 mM sodium chloride. Other process parameters were maintained constant in these experiments.

Redissolved Ps and CRM197 solutions were blended and mixed to target serotype-specific polysaccharide and protein concentrations. Sodium cyanoborohydride (1 moles per mole of polysaccharide repeating unit) was added, and conjugation proceeded for a serotype-specific duration. Reduction with sodium borohydride and final filtration were performed as described in Example 2.

Results

Figure 2:
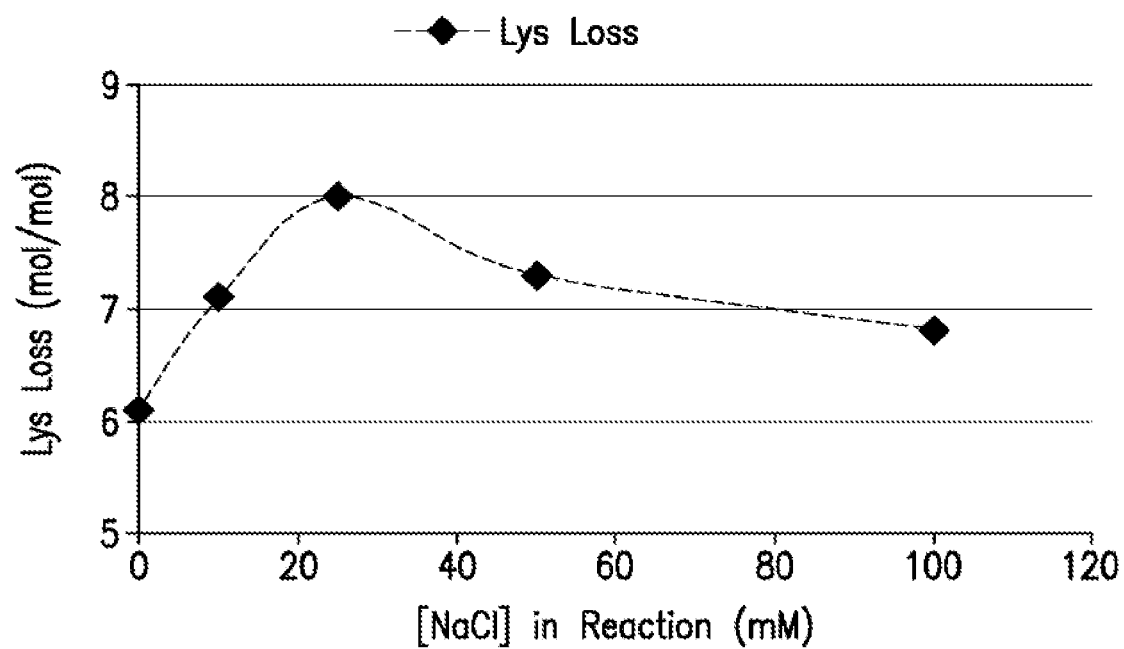
FIG. 2 demonstrates the impact of sodium chloride on lysine consumption for S. pneumoniae polysaccharide from serotype 20.
Figure 3:
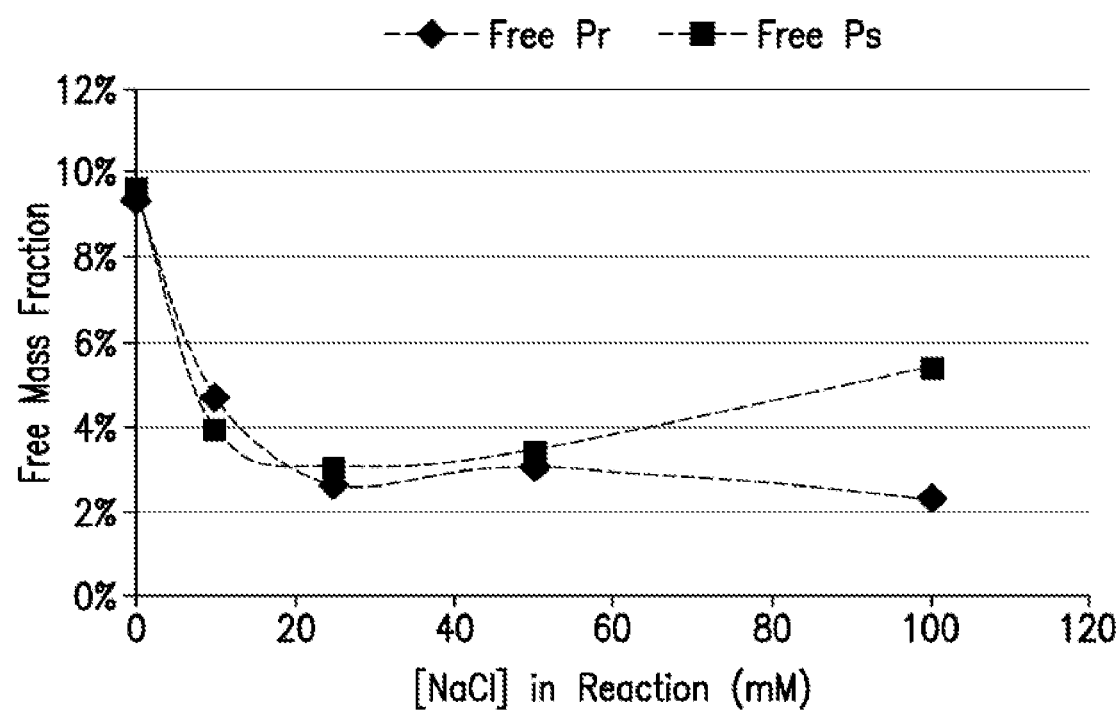
FIG. 3 demonstrates the impact of sodium chloride on free Ps and Pr for S. pneumoniae polysaccharide from serotype 20.

Experimental results for polysaccharide from S. pneumoniae serotype 20 showing the impact of sodium chloride during conjugation on conjugate attributes are shown in FIGS. 1, 2, and 3. Experimental results for S. pneumoniae serotypes 16F and 24F are shown in Table 8.

As shown in FIG. 1 for serotype 20, increasing sodium chloride concentration during conjugation (up to ca. 50 mM) increased conjugate size. As shown in FIG. 2, increasing sodium chloride concentration (up to ca. 25 mM) increased lysine consumption, and as shown in FIG. 3, increasing sodium chloride concentration (up to ca. 50 mM) decreased free Ps and free Pr.

TABLE 8

Impact of sodium chloride on conjugate attributes for S. pneumoniae serotypes 16F and 24F

| Serotype | NaCl Concentration During Conjugation (mM) | Conjugate Mn/Mw (kD) | Lysine Consumption (mol/mol) | Free Ps Fraction | Free Pr Fraction |
|---|---|---|---|---|---|
| 16F | 0 | 438/1040 | 9.3 | 23% | 7% |
| | 25 | 1161/3944 | 11.0 | 7% | 4% |
| 24F | 0 | 2534/6478 | 1.8 | 85% | 24% |
| | 25 | 2059/3402 | 4.5 | 59% | 10% |
| 15A | 0 | 954/1343 | 7.8 | 51% | 23% |
| | 25 | 1748/3371 | 8.9 | 23% | 7% |
| 35B | 0 | | | N/R | >32% |
| | 25 | | | 32% | 5% |

As shown in Table 8 for serotype 16F, inclusion of 25 mM sodium chloride during conjugation increased conjugate size and lysine consumption, while decreasing free Ps and free Pr. As shown in Table 8 for serotype 24F, inclusion of 25 mM sodium chloride during conjugation increased lysine consumption, while decreasing free Ps and free Pr.

Similar results were found for serotypes 15A and 35B. For serotype 15A, inclusion of 25 mM sodium chloride during conjugation increased conjugate size and lysine consumption, while decreasing free polysaccharide and free protein compared to no salt during conjugation. For serotype 35B, inclusion of 25 mM sodium chloride during conjugation increased conjugate size and lysine consumption (data not shown), while decreasing free protein compared to no salt during conjugation.

Effect of Salt Type and Concentration on Conjugation of S. pneumoniae Serotype 17F Using Reductive Amination in DMSO Activated serotype 17F polysaccharide was formulated for lyophilization at 6 mg Ps/mL with sucrose concentrations of 5% w/v in polypropylene containers. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved in DMSO. For some arms, concentrated salt solutions were spiked into the redissolved Ps solution or the Ps-CRM blend to achieve final concentrations during conjugation of 1-100 mM salt. Stock solutions used included 1M or 5M sodium chloride, 1M or 3M potassium chloride and 1M magnesium chloride. Other process parameters were maintained constant in these experiments.

Redissolved Ps and CRM197 solutions were blended and mixed to 2.7 g Ps/mL and 1.8 mg CRM197/mL. Sodium cyanoborohydride (1 moles per mole of polysaccharide repeating unit) was added, and conjugation proceeded for 1 hour. Sodium borohydride (2 mole per mole of polysaccharide repeating unit) was added following the conjugation reaction. The batch was diluted into 150 mM sodium chloride with approximately 0.025% (w/v) polysorbate 20, at approximately 4° C. Potassium phosphate buffer was then added to neutralize the pH.

Conjugates were then dialyzed against 150 mM sodium chloride with 0.05% (w/v) polysorbate 20 at approximately 4° C. using a 300 kDa NMWC membrane. The final conjugate solution was dispensed into aliquots and maintained at 4° C.

Results

The results are shown in Table 9. 2% is the limit of detection.

| Salt Conc. (mM) | Salt Type | Conjugate Mn (kD) | Conjugate Mw (Kd) | % Free Ps | Lysine Consumption (mol/mol) | % Free Protein |
|---|---|---|---|---|---|---|
| 0 | N/A | 966 | 1419 | 8% | 6.5 | 7% |
| 1 | NaCl | 1041 | 1671 | 10% | 8.1 | 6% |
| 2 | NaCl | 1318 | 2113 | 10% | 7.8 | 5% |
| 5 | NaCl | 1964 | 2933 | 5% | 8.8 | 3% |
| 10 | NaCl | 2407 | 3640 | 8% | 9.4 | 2% |
| 12.5 | NaCl | 2529 | 3749 | 7% | 9.6 | <2% |
| 25 | NaCl | 2657 | 3772 | 4% | 8.8 | 4% |
| 50 | NaCl | 3036 | 4198 | 3% | 9.5 | <2% |
| 100 | NaCl | 3031 | 4249 | 3% | 9.4 | <2% |
| 0 | N/A | 1012 | 1339 | 9% | 6.8 | 7% |
| 1 | KCl | 1189 | 1653 | 9% | 7.0 | 6% |
| 2 | KCl | 1533 | 2018 | 5% | 7.5 | 4% |
| 5 | KCl | 1862 | 2474 | 4% | 8.7 | 3% |
| 10 | KCl | 2416 | 3278 | 6% | 9.1 | 3% |
| 12.5 | KCl | 2654 | 3532 | 4% | 9.2 | 2% |
| 25 | KCl | 2641 | 3446 | 3% | 9.6 | 3% |
| 0 | N/A | 900 | 1335 | 9% | 6.3 | 7% |
| 25 | MgCl2 | 2878 | 4361 | 9% | 8.2 | 16% |
| 50 | MgCl2 | 1374 | 1994 | 12% | 6.6 | 18% |
| 100 | MgCl2 | 798 | 1175 | 29% | 4.0 | 34% |

For sodium chloride and potassium chloride conditions, increasing salt concentration during conjugation increased conjugate size and lysine consumption and decreased free Ps and free Pr. These effects plateaued at approximately 12.5 mM for both salt types. 25 mM and 50 mM magnesium chloride showed an increase in conjugate size and lysine consumption compared to the no salt condition. However, there seems to be increased free polysaccharide and free protein levels, and decreased extent of conjugation (measured by lysine loss and conjugate size) with increasing concentration of magnesium chloride from 25 mM to 100 mM. Therefore, it may be preferred to keep magnesium chloride in the concentration range of 0-50 mM.

Example 6: Formulation of Monovalent Conjugates

Pneumococcal polysaccharide-CRM197 conjugates were prepared as described in Examples 2-5. The required volume of bulk conjugates needed to obtain the target concentration of individual serotypes were calculated based on batch volume and concentration of individual bulk polysaccharide concentrations. Individual serotypes (12F, 15A, 16F, 17F, 23A, 23B, 24F, 31, and 35B) were combined with excipients, sterile filtered and added to APA under mixing conditions. The final concentration of each monovalent conjugate vaccine was 4 □g/mL (w/v PnPs) with 20 mM Histidine, 150 mM NaCl, 0.2% (w/v) PS-20 and 0.250 mg/mL (w/v Al) in the form of APA.

Example 7: Monovalent Conjugate New Zealand White Rabbit Immunogenicity Study (15A, 16F, 17F, 23A, 23B, 24F, 31, and 35B)

The immunogenicity of the monovalent conjugates was evaluated in a New Zealand White Rabbit (NZWR) model. Adult New Zealand White rabbits (NZWR, n=3/group) were intramuscularly (IM) immunized with 0.25 ml of respective monovalent conjugate vaccine on day 0 and day 14 (alternating sides). Monovalent pneumococcal vaccine was dosed at 1 μg PnPs (15A, 16F, 17F, 23A, 23B, 24F, 31, or 35B, each conjugated to CRM197) with 62.5 μg aluminum phosphate adjuvant (APA) per immunization. Sera were collected prior to study start (pre-immune) and on days 14 (post-dose 1, PD1) and 28 (post-dose 2, PD2). NZWRs were observed at least daily by trained animal care staff for any signs of illness or distress. The vaccine formulations in NZWRs were deemed to be safe and well tolerated. All animal experiments were performed in strict accordance with the recommendations in the Guide for Care and Use of Laboratory Animals of the National Institutes of Health. The NZWR experimental protocol was approved by the Institutional Animal Care and Use Committees at both Merck & Co., Inc (Kenilworth, NJ) and Covance (Denver, PA).

NZWR sera were tested in ELISA assays to evaluate IgG immunogenicity using a 1-2 mg/ml respective PnPs coating concentration. Functional antibody was determined through opsonophagocytosis assays (OPA) based on previously described protocols. See, e.g., Caro-Aguilar et al., 2017, Vaccine 35:865-72 and Burton et al., 2006, Clin Vaccine Immunol 13(9):1004-9.

All monovalent pneumococcal conjugate vaccines were found to be immunogenic in rabbits and generate functional antibody which killed the respective bacterial strain (data not shown). Serotype 12F was found to be immunogenic in mice (data not shown).

What is claimed is:

1. A method for preparing a *Streptococcus pneumoniae* (*S. pneumoniae*) polysaccharide-protein conjugate wherein the polysaccharide is a 15A, 16F, 17F, 20, 24F and a 35B polysaccharide and the protein is CRM197, the method comprising providing the polysaccharide within a first solution to react with the protein within a second solution to form a third solution in which a polysaccharide-protein conjugation reaction takes place to form the polysaccharide-protein conjugate, wherein the third solution contains an aprotic solvent and comprises 10 mM to 100 mM sodium chloride.

2. The method of claim 1, wherein the concentration of sodium chloride in the third solution is from 25 to 100 mM.

3. The method of claim 1, wherein the salt sodium chloride is present in the first solution.

4. The method of claim 1, wherein the salt sodium chloride is present in the second solution comprising the protein.

5. The method of claim 1, wherein the first solution and second solution are the same.

6. The method of claim 1, wherein the aprotic solvent is DMSO.

7. The method of claim 1, wherein the conjugation reaction is a Schiff base reduction or reductive amination.

* * * * *